US006486943B1

(12) United States Patent
Burns et al.

(10) Patent No.: US 6,486,943 B1
(45) Date of Patent: Nov. 26, 2002

(54) METHODS AND APPARATUS FOR MEASUREMENT AND CORRECTION OF OPTICAL ABERRATION

(75) Inventors: Stephen A. Burns, Reading, MA (US); Robert H. Webb, Lincoln, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 274 days.

(21) Appl. No.: 09/664,640

(22) Filed: Sep. 19, 2000

(51) Int. Cl.$^7$ .................................. G01B 9/00
(52) U.S. Cl. ........................ 356/124; 356/127
(58) Field of Search ............... 356/124, 125, 356/127, 614, 615, 622, 623, 124.5, 239.2

(56) References Cited

U.S. PATENT DOCUMENTS

| | | | |
|---|---|---|---|
| 4,490,039 A | 12/1984 | Bruckler et al. ............ | 356/121 |
| 4,518,854 A | 5/1985 | Hutchin ...................... | 250/201 |
| 4,725,138 A | 2/1988 | Wirth et al. ................. | 356/121 |
| 4,737,621 A | 4/1988 | Gonsiorowski et al. ..... | 250/201 |
| H615 H | 4/1989 | Feinleib et al. ............. | 356/121 |

(List continued on next page.)

FOREIGN PATENT DOCUMENTS

WO    WO 97/21989    6/1997

OTHER PUBLICATIONS

Investigative Ophthalmology and Visual Science, Feb. 15, 1996, vol. 37, No. 3.
Bille et al., Scanning Laser Tomography of the Living Eye, pp. 528–547, Barry R. Masters, Noninvasive Diagnostic Techniques in Ophthalmology, New York: Springer–Verlag, c1990.
Liang et al., Objective Measurement of Wave Aberrations of the Human Eye with the use of a Hartmann–Shack Wave–Front Sensor, Jul. 1994, J. Opt. Soc. Am. A., vol. 11, No. 7.
G. Walsh et al., Objective Technique for the Determination of monochromatic Aberrations of the Human Eye, SJ. Opt. Soc. Am. A., Sep. 1984, vol. 1 No. 9.
Dreher et al., Active Optical Depth Resolution Improvement of the Laser Tomographic Scanner, Applied Optics, Feb. 15, 1989, vol. 28, No. 4.

*Primary Examiner*—Georgia Epps
*Assistant Examiner*—Jack Dinh
(74) *Attorney, Agent, or Firm*—Testa, Hurwitz & Thibeault LLP

(57) ABSTRACT

The invention relates to methods and apparatus for determining a characteristic of an optical element. The apparatus includes a spatial light pattern generator adapted to generate a beam of light at a predetermined spatial position, at least one lenslet disposed in an array of lenslets adapted to receive the beam of light from the spatial light pattern generator, and to direct the beam of light to the optical element. The apparatus further includes a detector positioned to receive the beam of light subsequent to the beam of light encountering the optical element. The detector is adapted to detect a received spatial position at which the detector receives the beam of light. The apparatus also includes a processor adapted to compare the predetermined spatial position with the received spatial position to determine the characteristic of the optical element. The invention further relates to methods and apparatus for generating a diffraction limited image. The apparatus includes a spatial light pattern generator adapted to generate a plurality of beams of light at selected spatial positions to compensate for a characteristic of an optical element and an array of lenslets adapted to receive the plurality of beams of light from the spatial light pattern generator and to direct the plurality of beams of light to the optical element. The apparatus also includes an image plane positioned to receive the plurality of beams of light subsequent to the plurality of beams of light encountering the optical element and adapted to form the diffraction limited image.

62 Claims, 11 Drawing Sheets

OTHER PUBLICATIONS

| | | | |
|---|---|---|---|
| 5,120,128 A | 6/1992 | Ulich et al. | 356/121 |
| 5,164,578 A | 11/1992 | Witthoft et al. | 250/201.9 |
| 5,177,511 A | 1/1993 | Feuerstein et al. | 351/205 |
| 5,233,174 A | 8/1993 | Zmek | 250/201.9 |
| 5,258,791 A | 11/1993 | Penney et al. | 351/211 |
| 5,396,364 A | 3/1995 | O'Meara et al. | 359/292 |
| 5,455,645 A | 10/1995 | Berger et al. | 351/223 |
| 5,557,352 A | 9/1996 | Nordquist | 351/237 |
| 5,629,765 A | 5/1997 | Schmutz | 356/121 |
| 5,662,401 A | 9/1997 | Shimizu et al. | 353/38 |
| 5,684,561 A | 11/1997 | Yancey | 351/209 |
| 5,696,371 A | 12/1997 | Meyers | 250/208.1 |
| 5,777,719 A | 7/1998 | Williams et al. | 351/212 |
| 5,785,704 A | 7/1998 | Bille et al. | 606/17 |
| 5,873,832 A | 2/1999 | Maloney et al. | 600/473 |
| 5,875,019 A | 2/1999 | Villani | 351/211 |
| 5,912,731 A | 6/1999 | DeLong et al. | 356/121 |
| 5,949,521 A | 9/1999 | Williams et al. | 351/246 |
| 5,953,101 A | 9/1999 | Nordquist | 351/211 |
| 6,004,313 A | 12/1999 | Shimmick et al. | 606/5 |
| 6,007,204 A | 12/1999 | Fahrenkrug et al. | 351/221 |
| 6,199,986 B1 * | 3/2001 | Williams et al. | 351/221 |
| 6,271,914 B1 * | 8/2001 | Frey et al. | 356/124 |
| 6,338,559 B1 * | 1/2002 | Williams et al. | 351/212 |

* cited by examiner

METHODS AND APPARATUS FOR MEASUREMENT AND CORRECTION OF OPTICAL ABERRATION

GOVERNMENT SUPPORT

This invention was made with government support under Contract Number EYO4395, awarded by the National Eye Institute. The Government may have certain rights in the invention.

FIELD OF THE INVENTION

The invention relates to the field of instrumentation for optical measurements and more specifically to methods and devices for measuring and correcting for optical aberrations in an optical system.

BACKGROUND OF THE INVENTION

A typical optical system operates on an incident optical wavefront to transform it to a different optical wavefront. Generally, different points on the wavefront experience different transformations depending on what portions of the optical system they encounter. For example, when a wavefront is incident on a lens, those portions of the wavefront that traverse the periphery of the lens will experience phase delays which differ from those experienced by portions of the wavefront which traverse the center of the lens. A wavefront can be defined as a plurality of points having a constant phase. The wavefront encountering the lens results in a transmitted wavefront having a different shape. Appropriately shaping and positioning lenses can modify a transmitted wavefront to a desired shape.

In some cases, an optical system is known to produce an undesired transformation. One way to correct the transformation is to add a second optical system designed to correct for the deficiencies of the original optical system. For example, in the case of a human eye requiring a corrective lens, the optical components of the human eye perform an optical transformation which is imperfect. In another example, a flawed objective lens installed in a large telescope performs an imperfect transformation. Rather than replacing the objective lens, it may by preferable to install a corrective lens. In both of these cases, it is necessary to know characteristics of the flawed optical transformation in order to correct it.

One method for measuring the optical characteristics of a human eye is the technique of placing lenses having various correction factors in front of the eye and asking the patient whether or not the overall image has improved. Using this substitution technique, one can determine an overall correction for the optical characteristics of the eye. An instrument that is generally used to approximate an optical system that corrects for the flawed optical transformation of an eye is referred to as a "refractometer." In the case of a general lens system, corrections are determined by a variety of tests, each referred to by its owns name, such as the "Foucault test." Throughout the following description, the term "refractometer" will be used to refer to all of the instruments that perform such tests.

A mathematical model of the eye can be expressed in terms of a polynomial equation. One such mathematical model is known as the Siedel model. The substitution technique described above determines the overall correction for the eye, but it is limited to prismatic, cylindrical, and spherical corrections. These corrections provide only the lowest-order terms of the Siedel or polynomial model of the eye's optical system. The technique does not correct for the errors that are specified by higher-order terms of the polynomial model. Additionally, it is not possible to obtain point-by-point measurements of the wavefront at designated sites on the optical system using the technique. For example, where the optical system is a cornea, this technique cannot determine the optimal wavefront portion at each point on the cornea.

A number of refractometers have been developed that are designed to determine the optimal wavefront at designated sites on the optical system. For example, one such optical system includes a reference optical subsystem for projecting a reference pattern on the patient's retina through a reference area on the cornea and a separate measurement optical subsystem for projecting a measurement pattern on the patient's retina through a measurement area on the cornea.

To determine the shape of the optimal wavefront at a designated site on the cornea using this refractometer, the measurement pattern is moved across the retina until its location coincides with the location of the reference pattern. Based on the difference between the initial and final positions of the measurement pattern, this refractometer can infer the correction of the wavefront required at the selected corneal site.

An example of another refractometer consists of two optical subsystems aligned along substantially the same optical axis: a reference optical subsystem and a measurement optical subsystem. The reference optical subsystem projects a reference pattern onto a reference pattern position on a detector plane through a selected reference site on the measurement plane. The measurement optical subsystem projects a measurement pattern onto a measurement pattern position on the detector plane through a selected measurement site on the measurement plane. The two subsystems may have some or all of their elements in common.

In operation, the location of the measurement pattern on the detector can be controlled by an observer through the use of an optical aligner coupled to the measurement optical subsystem. Using the optical aligner, the observer can move the measurement pattern on the detector until it is aligned with the reference pattern on the detector. The distance and the direction in which the observer moves the measurement pattern in order to align it with the reference pattern provide a measure of the shape of the optimal wavefront associated with the portion of the wavefront incident on the selected measurement site on the measurement plane. This method is sometimes referred to the "nulling" method.

In an alternate operation, a measurement of the displacement of the measurement pattern from the reference pattern is used to characterize the wavefront. This method is sometimes referred to the "non-nulling" method.

Although the devices disclosed above can be used to measure the deviation from the shape of an optimal wavefront at a selected measurement site on the optical system, they are complex and they do not provide an observation of the optical system after correction.

SUMMARY OF THE INVENTION

The invention relates to an apparatus for determining a characteristic of an optical element. In one embodiment, the apparatus includes a spatial light pattern generator adapted to generate at least one beam of light at a predetermined spatial position. The apparatus further includes at least one lenslet disposed in an array of lenslets adapted to receive the at least one beam of light from the spatial light pattern generator, and to direct the at least one beam of light to the optical element. The apparatus further includes a detector positioned to receive the beam of light subsequent to the beam of light encountering the optical element, and adapted to detect a received spatial position at which the detector receives the beam of light. The apparatus further includes a processor adapted to compare the predetermined spatial position with the received spatial position to determine the characteristic of the optical element. In another embodiment, the processor is further adapted to change the predetermined spatial position in response to the received spatial position.

In another embodiment, the spatial light pattern generator includes an opaque mask having a movable aperture. In a further embodiment, the spatial light pattern generator includes a spatial light modulator. In yet another embodiment, the spatial light pattern generator includes an array of individually addressable light-modulating elements. In one embodiment, the array of lenslets is arranged in a substantially uniform pattern. In another embodiment, the uniform pattern is chosen from the group comprising substantially a square, a circle, a rectangle, an ellipse, and concentric circles. In yet another embodiment, the detector is chosen from a group of position detectors, including a retina, an array detector, a quadrant detector, a photodetector, a photodiode, a charge coupled device (CCD) detector, and a photosensitive film. In one embodiment, the optical element comprises an eye, a lens, a mirror, a spherical mirror, a segmented mirror, and a flexible mirror. In one embodiment, the processor includes a computer or control electronics. In another embodiment, the apparatus further includes a contact lens fabrication device coupled to the processor. In another embodiment, the apparatus further includes an intraocular lens fabrication device coupled to the processor. In yet another embodiment, the apparatus fiuther includes laser surgical equipment coupled to the processor. In other embodiments, the characteristic includes wavefront aberration, defocus, astigmatism, and curvature.

The invention also relates to a method for determining a characteristic of an optical element. The method includes passing at least one beam of light originating from a predetermined spatial position through a lenslet in an array of lenslets to the optical element. Subsequent to said at least one beam of light encountering said optical element, the method further includes detecting the at least one beam of light at a received spatial position, and comparing the predetermined spatial position with the received spatial position to determine the characteristic of the optical element. The method further includes the step of processing the received spatial position to determine the characteristic of the optical element. The method also includes providing a detector. The detector is chosen from the group comprising a retina, a photodetector, a quadrant detector, a charge coupled device, and a photosensitive film. In another embodiment, the step of passing at least one beam of light includes providing a spatial light pattern generator. In yet another embodiment, the step of comparing the predetermined spatial position with the received spatial position includes providing a processor. In another embodiment, the method further includes the step of changing the predetermined spatial position in response to the received spatial position.

The invention also relates to an apparatus for generating a diffraction limited image. In one embodiment, the apparatus includes a spatial light pattern generator adapted to generate a plurality of beams of light at selected spatial positions to compensate for a characteristic of an optical element. The apparatus further includes an array of lenslets adapted to receive the plurality of beams of light from the spatial light pattern generator and to direct the plurality of beams of light to the optical element. The apparatus also includes an image plane positioned to receive the plurality of beams of light subsequent to the plurality of beams of light encountering the optical element and adapted to form the diffraction limited image. In one embodiment, each of the plurality of beams of light is coherent with respect to the others of the plurality of beams of light.

In another embodiment, the spatial light pattern generator includes an opaque mask having a movable aperture. In a further embodiment, the spatial light pattern generator includes a spatial light modulator. In yet another embodiment, the spatial light pattern generator includes an array of individually addressable light-modulating elements. In one embodiment, the array of lenslets is arranged in a substantially uniform pattern. In another embodiment, the uniform pattern is chosen from the group comprising substantially a square, a circle, a rectangle, a triangle, an ellipse, a pentagon, a hexagon, an octagon and concentric circles. In yet another embodiment, the detector is chosen from the group including a retina, an array detector, a quadrant detector, a photodetector, a photodiode, a charge coupled device (CCD) detector, and a photosensitive film. In one embodiment, the optical element comprises an eye, a lens, a mirror, a spherical mirror, a segmented mirror, and a flexible mirror. In one embodiment, the processor includes a computer or control electronics. In another embodiment, the apparatus further includes a contact lens fabrication device coupled to the processor. In another embodiment, the apparatus further includes an intraocular lens fabrication device coupled to the processor. In yet another embodiment, the apparatus further includes laser surgical equipment coupled to the processor. In other embodiments, the characteristic includes wavefront aberration, defocus, astigmatism, and curvature.

The invention also relates to a method for generating a diffraction limited image. The method includes passing a plurality of beams of light through a lenslet array to an optical element, the plurality of beams of light originating from selected spatial positions to compensate for a characteristic of the optical element. Subsequent to said plurality of beams of light encountering the optical element, the method further includes imaging the plurality of beams of light to form a diffraction limited image. In one embodiment, each of the plurality of beams of light is coherent with respect to the others of the plurality of beams of light.

In another embodiment, the step of imaging includes providing a detector. The detector is chosen from the group comprising a retina, a photodetector, a quadrant detector, a charge coupled device, and a photosensitive film. In another embodiment, the step of passing a plurality of beams of light comprises providing a spatial light pattern generator. In yet another embodiment, the step of imaging comprises providing a processor.

BRIEF DESCRIPTION OF THE DRAWINGS

The foregoing and other objects, features and advantages of the invention will be apparent from the following description taken in conjunction with the accompanying drawings, in which.

DETAILED DESCRIPTION

Figure 1A:
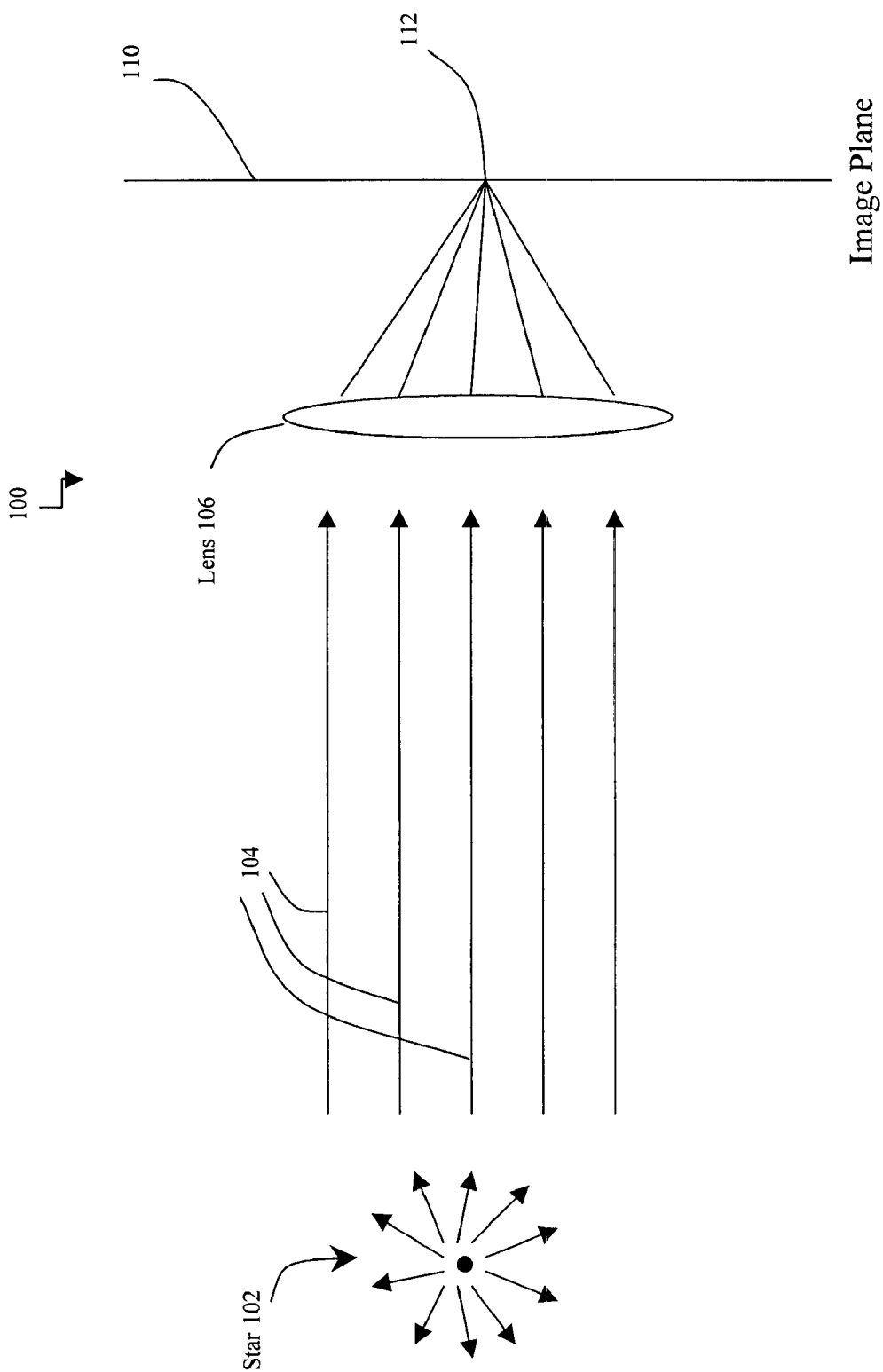
FIG. 1A is a schematic diagram showing an illustrative ray trace for an ideal optical system.

Typical optical imaging systems are designed to focus distant objects on an image plane. For example, a camera images objects through its lens system onto a light sensitive film in the image plane of the lens system. If the imaging system was ideal, then all of the rays of light entering the system from a distant object such as a star, would be imaged onto the same position on the image plane. In that case, only diffraction from the aperture of the imaging system would limit the sharpness or accuracy of the image. FIG. 1A is a conceptual diagram of such an ideal imaging system 100. A distant object 102 (i.e., a star) is very far away from the imaging system 100. Since there is a large distance between the object 102 and the lens 106, the rays 104 arrive at the lens 106 substantially parallel to each other. If the lens 106 is an ideal lens, it focuses the rays 104 down to the point 112 on the image plane 110. In a non-ideal system, optical aberrations exist that limit the ability of the imaging system in such systems. In these non-ideal systems, rays of light entering the imaging system at different points are imaged onto different locations of the image plane.

Figure 1B:
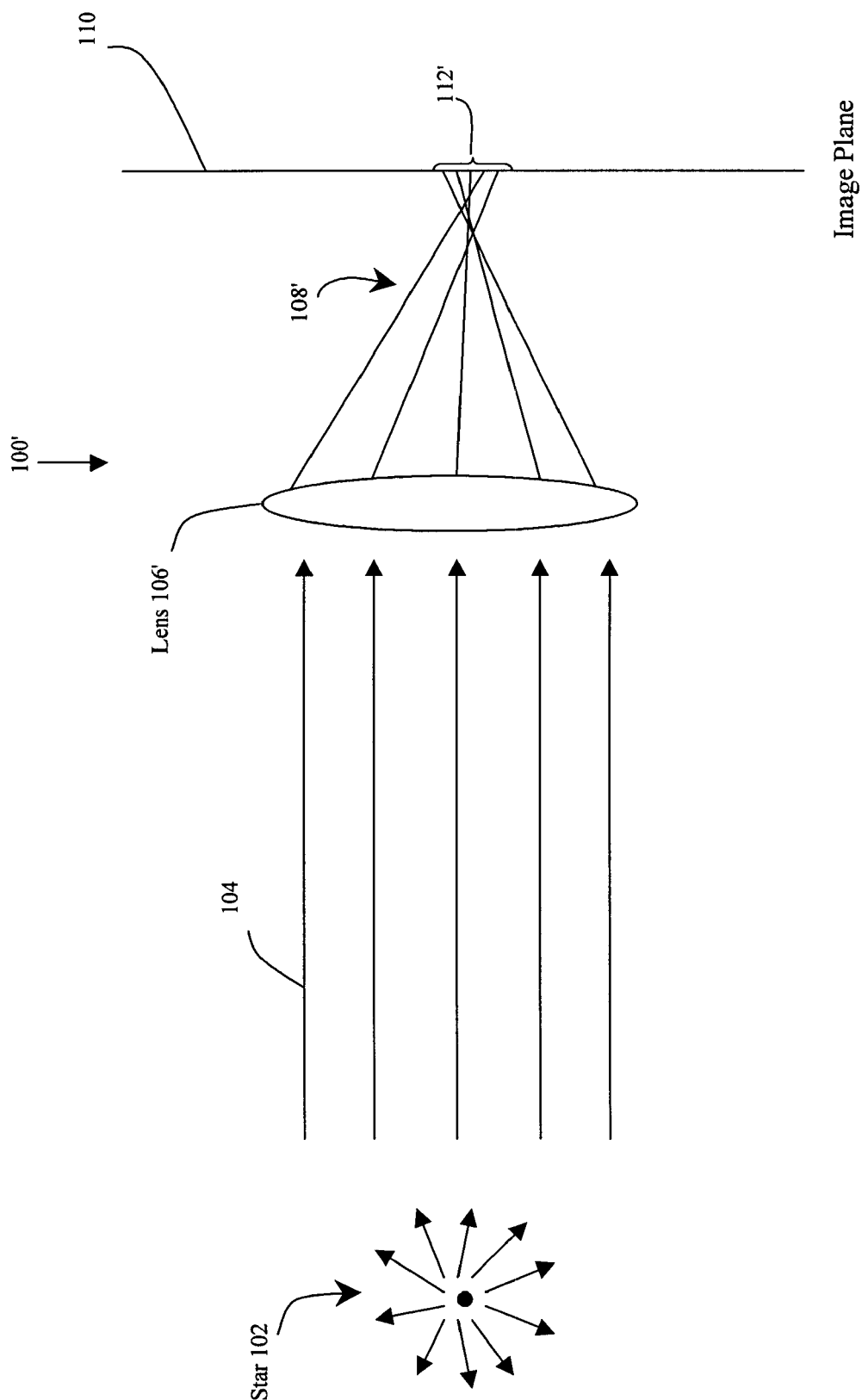
FIG. 1B is a schematic diagram showing an illustrative ray trace for an imperfect optical system.

FIG. 1B is a conceptual diagram of an aberrated imaging system 100'. As in the case of FIG. 1A, the distant object 102 is very far away from the imaging system 100'. The rays 104 arrive at the lens 106' substantially parallel to each other. Due to the imperfect lens 106', the transmitted rays 108' impinge on the image plane 110 at different locations 112' creating a blurred image on the image plane 110. Blurring of the image can also result from the improper placement of the lens 106' with respect to the image plane 1 10.

Figure 1C:
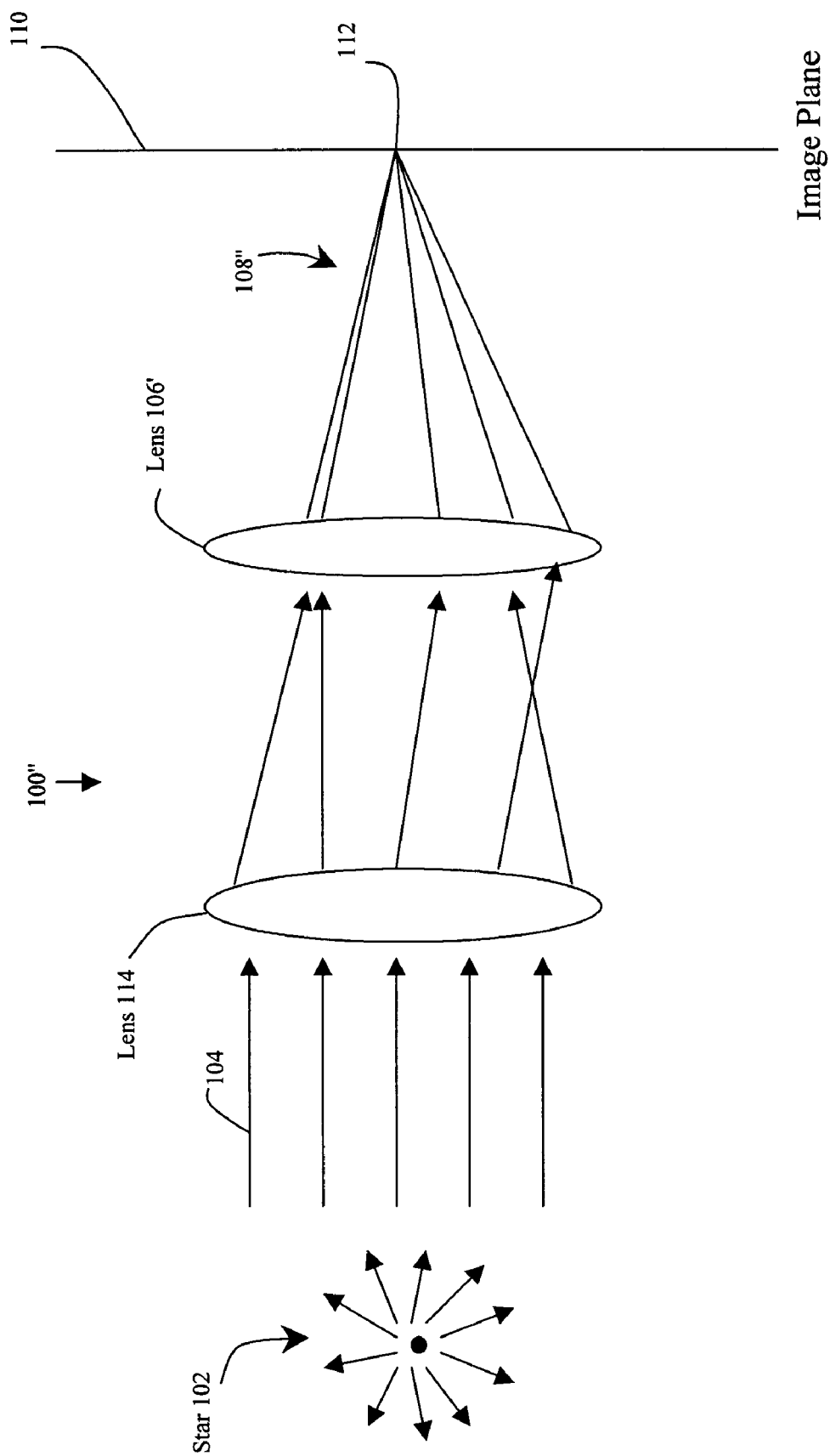
FIG. 1C is a schematic diagram showing an illustrative compensated ray trace for the imperfect optical system of FIG. 1B.

FIG. 1C is a conceptual diagram showing a compensated ray trace for the imperfect optical system of FIG. 1B. As in FIGS. 1A and 1B, the distant object 102 is very far away from the imaging system 100". The rays 104 arrive at the correction lens 114 substantially parallel to each other. The correction lens 114 is configured to compensate for the imperfect lens 106'. The transmitted rays 108" impinge on the image plane 110 at the point 112 on the image plane 110. Although the following description is in terms of the ray description of light, skilled artisans will also appreciate that aspects of the invention can be understood using a wave analysis. Although the previous figures are described in terms of lenses, skilled artisans will appreciate that other optical elements such as mirrors can be used.

Figure 2A:
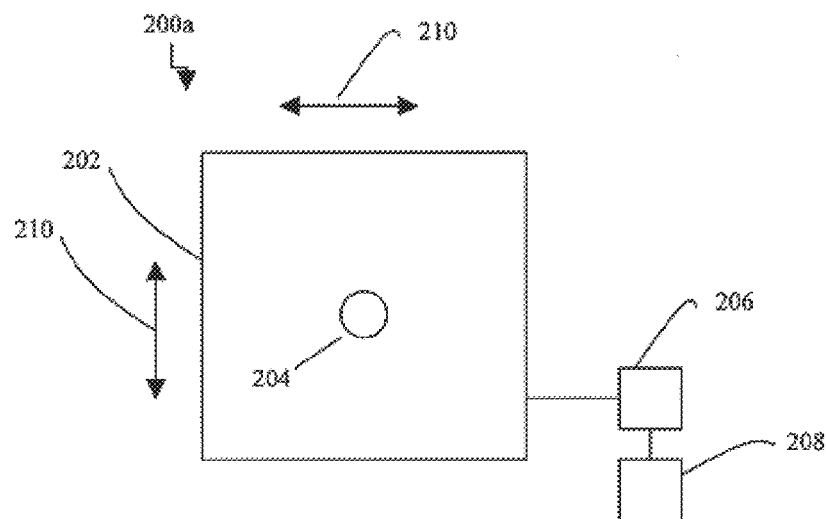
FIG. 2A is a conceptual diagram of a spatial light pattern generator according to an illustrative embodiment of the invention.

FIG. 2A is a conceptual diagram of a spatial light pattern generator 200a according to an illustrative embodiment of the invention. A spatial light pattern generator, as used in the specification, refers to any device that changes a property of light, such as brightness, according to a spatially variable pattern and includes, for example, holes in an opaque masking material, electronically addressable transmissive or reflective arrays, and light sources having controllable brightness patterns. In one embodiment, a spatial light pattern generator is referred to as a spatial light modulator (SLM). In the embodiment shown in FIG. 2A, the spatial light pattern generator 200a has a moveable site-selecting aperture 204. The movable aperture 204 is movable within an opaque screen 202. The movable aperture 204 is implemented by coupling a stepper motor 206 to an aperture controller 208 and the opaque screen 202. In response to a signal to the aperture controller 208, the stepper motor 206 translates the opaque screen 202 including the aperture 204 in the site-selection plane 210.

Figure 2B:
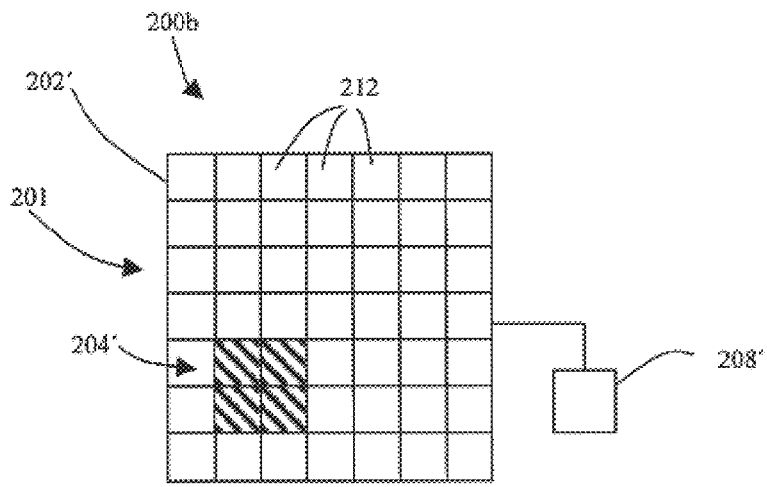
FIG. 2B is a conceptual diagram of a spatial light pattern generator according to another illustrative embodiment of the invention.

FIG. 2B illustrates another embodiment of a spatial light pattern generator 200b. In this embodiment, a spatial light modulator 201 having a plurality of light-modulating elements 212 is shown. In one embodiment, the spatial-light modulating elements are coherent with respect to each other. Each light-modulating element 212 can be switched between an "ON" state and an "OFF" state. One or more light-modulating elements 212 form the aperture 204' whose size, shape and location on the opaque mask 202' can be controlled by the distribution of lightz modulating elements 212 forming the mask 202'. In one embodiment, controller 208' controls the light-modulating elements 212. In another embodiment, the light-modulating elements 212 are liquid crystals. In that case, the ON and OFF states correspond to the transmissive and opaque states of the liquid crystal for a particular polarization of light, respectively. In an alternative embodiment, the light-modulating elements 212 are movable micro-mirrors, in which the ON state corresponds to the position in which the micro-mirror reflects light at a suitable angle to the plane of the mask 202' and the OFF state corresponds to the position in which the micro-mirror deflects light away from the plane of the mask 202' corresponding to the ON state. Skilled artisans will appreciate that other types of spatial light modulators can be used without departing from the spirit and scope of the invention.

By utilizing a mask 202' having individually addressable light-modulating elements 212, apertures 204' of different sizes and shapes are formed. Such a mask 202' is not subject to mechanical stresses such as vibration as is the mask 202 of FIG. 2A.

Figure 2C:
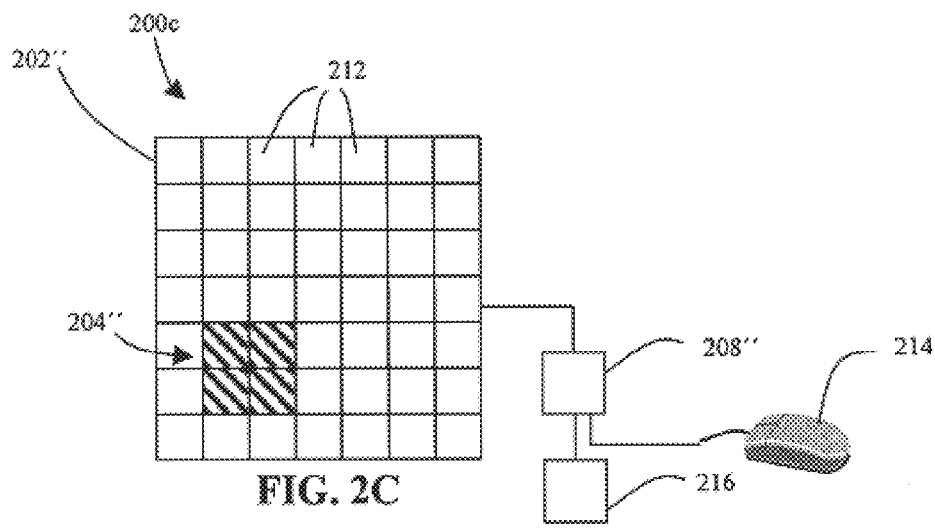
FIG. 2C is a conceptual diagram of a spatial light pattern generator according to a further embodiment of the invention.

FIG. 2C illustrates another embodiment of a spatial light modulator 200c according to the invention. This embodiment includes one or more light-modulating elements 212. The lightmodulating elements 212 form aperture 204" whose size, shape and location on the opaque mask 202" can be controlled by the distribution of light-modulating elements 212 forming the mask 202". In one embodiment, controller 208" controls the light-modulating elements 212 through the use of a pointing device 214. The pointing device 214, in one embodiment, is a computer mouse as shown in FIG. 2C. Alternatively, ajoystick, trackball, light pen, or other similar device is used to control the light-modulating elements 212. In an alternative embodiment, a processor 216 is adapted to control the controller 208". In another embodiment, the processor 216 controls the controller 208" through the use of a feedback loop which couples to a detector (not shown). In an alternative embodiment, the processor 216 records the various positions of the light-modulating elements 212. Alternatively, the processor 216 tracks the movements of the pointing device 214 by the user.

Figure 2D:
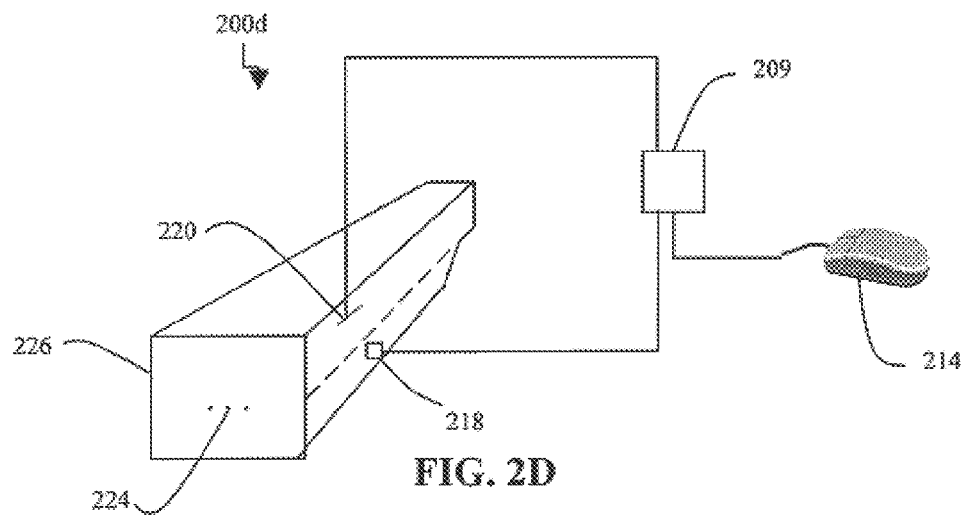
FIG. 2D is a conceptual diagram of a spatial light pattern generator according to an additional illustrative embodiment of the invention.

FIG. 2D illustrates a spatial light generator 200d of the form of a cathode ray tube 226. In this embodiment, the deflection of an electron beam 224 is under the control of the controller 209. The controller 209 couples to the elements 220 and 218. By manipulating the voltage in the elements 220 and 218, the controller 209 controls the electron beam 224. In an alternative embodiment, a pointing device 214 couples to the controller 209 for manipulating the electron beam 224.

Figure 2E:
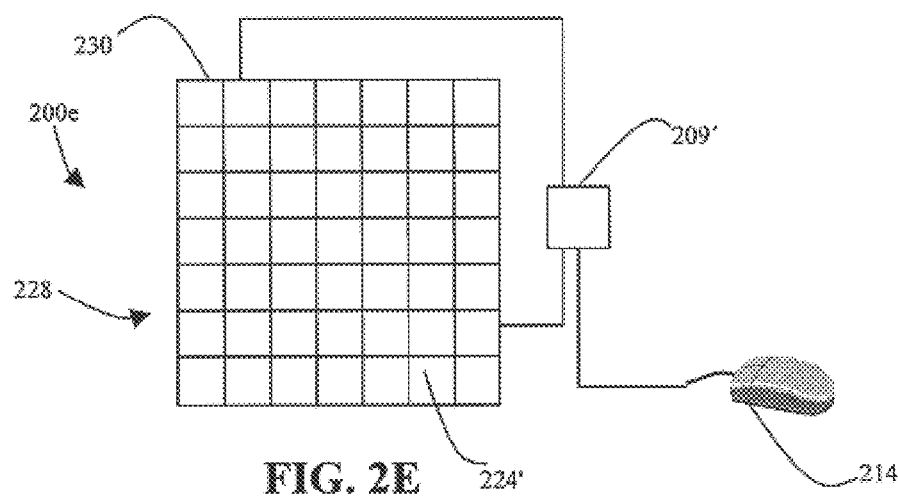
FIG. 2E is a conceptual diagram of a spatial light pattern generator according to another illustrative embodiment of the invention.

FIG. 2E illustrates a spatial light pattern generator 200e including an array 228 of individually addressable light emitting elements 230, such as light emitting diodes (LEDs). In this embodiment, the controller 209' controls which light emitting elements 230 in the array 228 are turned on. In an alternative embodiment, the pointing device 214 couples to the controller 209' and manipulates the state of the light emitting elements 230 in the array 228.

Figure 2F:
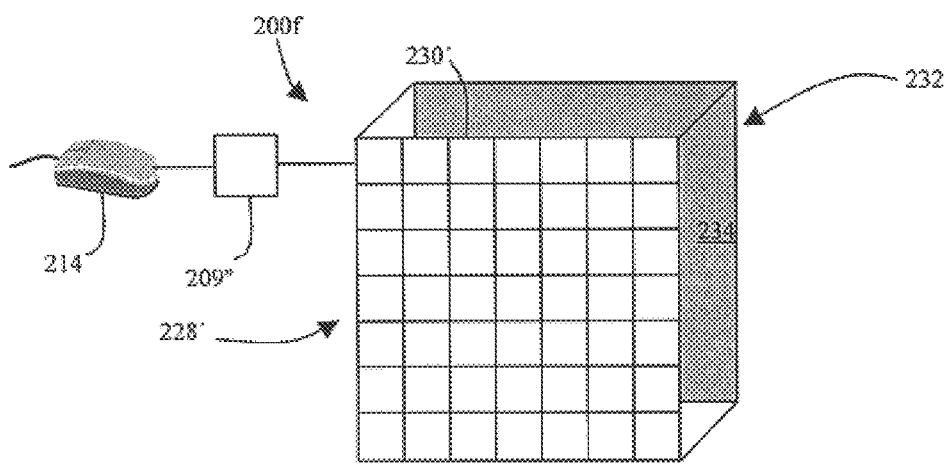
FIG. 2F is a conceptual diagram of a spatial light pattern generator according to a further illustrative embodiment of the invention.

FIG. 2F illustrates a spatial light pattern generator 200f including an illumination pattern source 232. The illumination pattern source 232 includes a uniform light source 234 and an array 228' of individually addressable light-modulating elements 230'. In this embodiment, the controller 209" controls which light-modulating elements 230' will block light generated by the uniform light source 232. In another embodiment, the pointing device 214 couples to controller 209" and manipulates the light-modulating elements 230'.

Figure 3A:
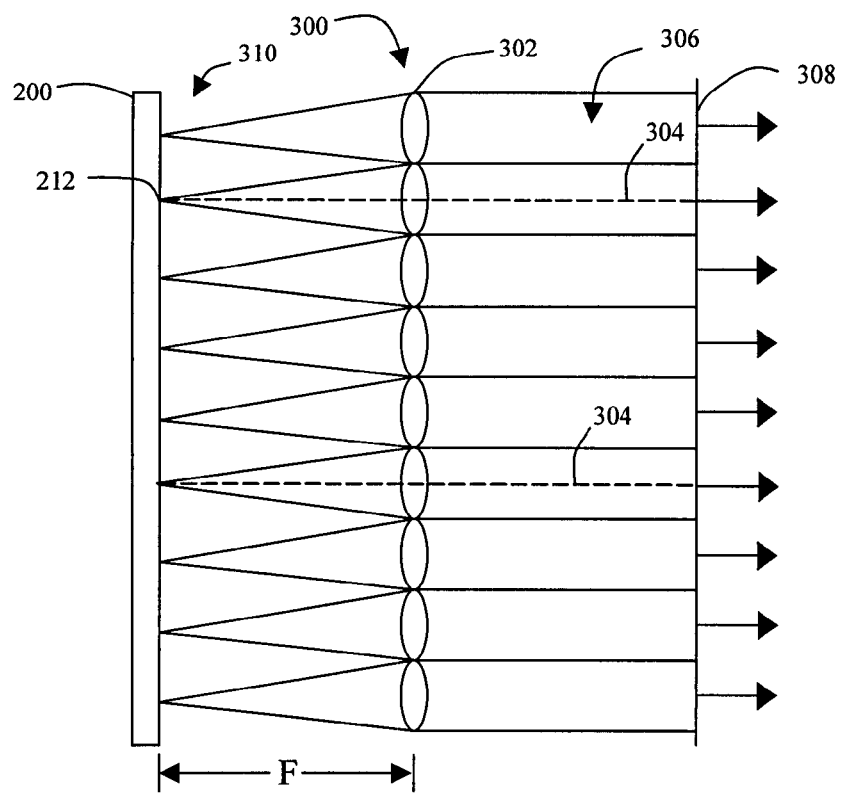
FIG. 3A depicts an array of lenslets in optical communication with a spatial light pattern generator according to one embodiment of the invention.

FIG. 3A illustrates a lenslet array 300 according to one embodiment of the invention. The lenslet array 300, in some instances, is referred to as a microoptics array. The lenslet array 300 is comprised of a plurality of lenslets 302 or lenslet elements, sometimes referred to as microlenses, and arranged in a substantially uniform pattern. In another embodiment, the pattern is not uniform. In one embodiment, the pattern is substantially square in shape. In another embodiment, the pattern is substantially rectangular. In still another embodiment, the pattern is substantially circular. In yet another embodiment, the pattern is substantially elliptical. In another embodiment, the pattern includes concentric lenslets. In other embodiments, a pentagonal, a hexagonal or an octagonal pattern is used. Skilled artisans will appreciate that any mathematically defined pattern could be used. Illustratively, each of the lenslets 302 is evenly separated from an adjacent lenslet 302. In operation, a spatial light pattern 310 generated by a spatial pattern generator 200 impinges on each lenslet 302. The spatial light pattern generator 200 is located at substantially a focal length F from the lenslets 302. In another embodiment, the distance between the spatial light pattern generator 200 and the lenslets 302 is less than the focal length F of the lenslets 302. In another embodiment, the distance between the spatial light pattern generator 200 and the lenslets 302 is greater than the focal length F of the lenslets 302. In one illustrative embodiment, the light-modulating elements 212 corresponding to the location of the optical axis 304 of each lenslet 302 in the lenslet array 300 are switched ON. This arrangement generates collimated light 306 from each lenslet 302 in the lenslet array 300. The collimated light 306 exhibits a perfectly planar wavefront 308 propagating away from the lenslet array 300. As the positions of light-modulating elements 212 are changed within the spatial light pattern generator 200, the wavefront 308 begins to distort. This distortion is shown in FIG. 3B.

Figure 3B:
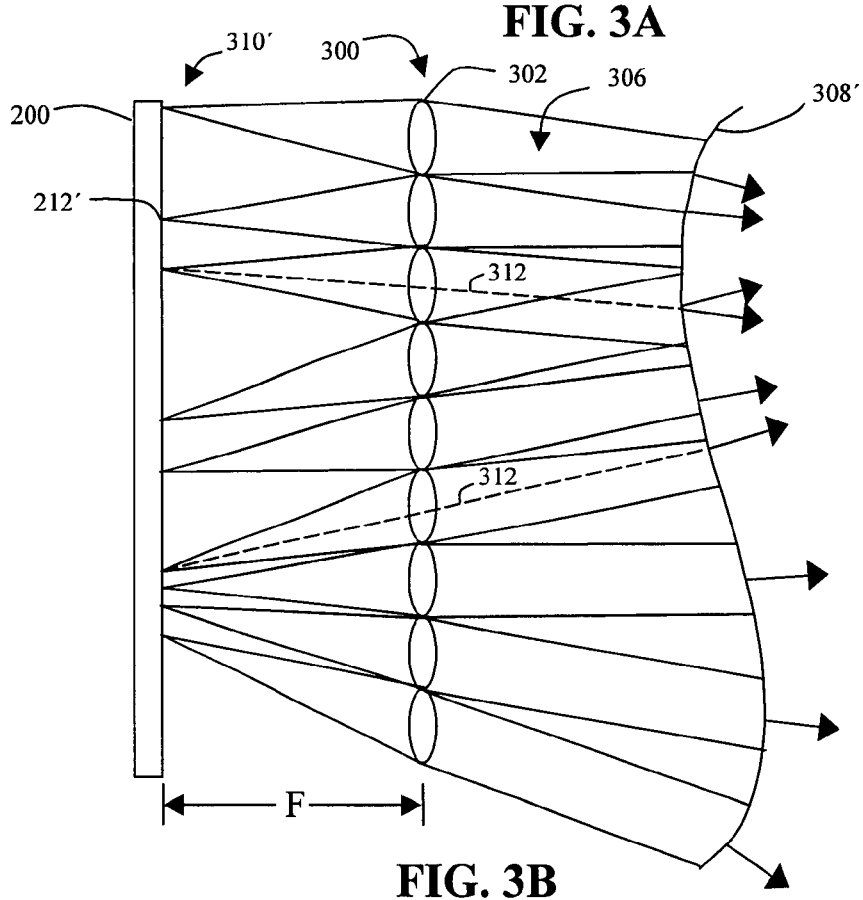
FIG. 3B depicts an array of lenslets in optical communication with a spatial light pattern generator according to another embodiment of the invention.

FIG. 3B illustrates the lenslet array 300 in optical communication with the spatial light pattern generator 200. In this embodiment, the positions of light-modulating elements 212' no longer correspond to the optic axis of each lenslet 302 in the lenslet array 300. In operation, a spatial light pattern 310' generated by a spatial pattern generator 200 impinges on each lenslet 302. The spatial light pattern generator 200 is substantially located at a focal length F from the lenslets 302. This arrangement generates substantially collimated light 306 from each lenslet 302 in the lenslet array 300. However, the collimated light 306 exiting from each lenslet 302 is tilted with respect to the optic axis of the lenslet 302. The wavefront 308' is no longer planar due to the deviated rays from the collimated beams 306. Skilled artisans will appreciate that the wavefront 308' is perpendicular to the rays 312 emanating from the lenslets 302.

In one embodiment, a corrective lens 106' (not shown) located to the right of the non-planar wavefront 308', effectively modifies the wavefront 308' to generate a substantially planar wavefront 308. In another typical embodiment, the corrective lens 106' is not ideal, causing the modified wavefront 308 to be non-planar. One embodiment of the invention as shown in FIG. 4 selectively modifies a wavefront to generate a desired wavefront.

Figure 4:
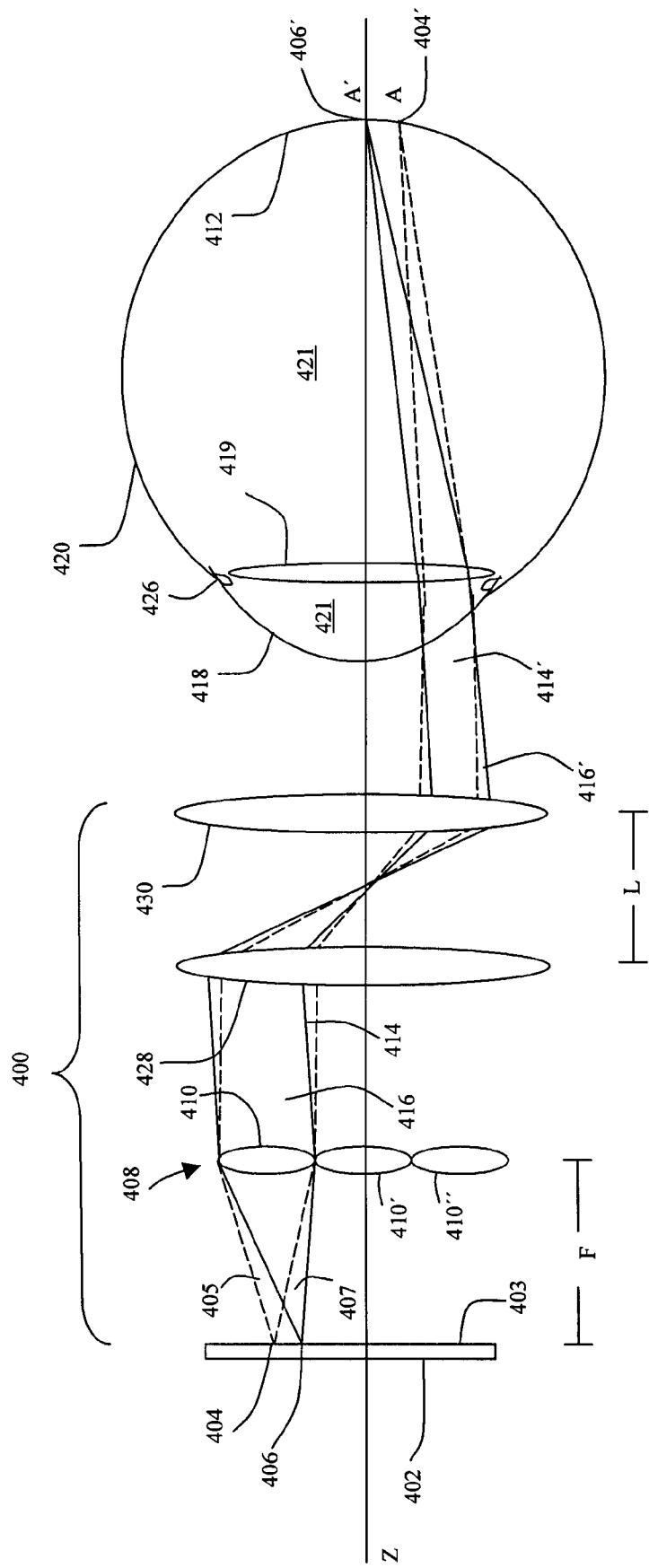
FIG. 4 is a schematic block diagram of an illustrative wavefront sensor for measuring characteristics of an eye according to one embodiment of the invention.

FIG. 4 illustrates a highly schematic block diagram of a wavefront sensor 400 for measuring characteristics of an eye 420 according to one embodiment of the invention. The wavefront sensor 400 is also referred to as a refractometer. The front surface 403 of the spatial light pattern generator 402 contains the light modulating elements 404 and 406. In one embodiment, the surface 403 is disposed in a plane perpendicular to axis Z of the refractometer 400. The lenslet array 408 comprises a plurality of evenly spaced lenslets 410 arranged in a planar configuration. In one embodiment, the lenslets 410 are arranged in a square array configuration. In another embodiment, the lenslets 410 are arranged in a radial configuration. In another embodiment, the lenslets 410 are arranged in a hexagon al configuration. In other embodiments, the lenslets 410 are arranged in any geometric or random pattern. In yet another embodiment, the positions of the lenslets 410 with respect to each other is varied. In an illustrative embodiment, the lenslet array 408 is disposed in the plane perpendicular to axis Z of the refractometer 400. The light modulating elements 404 and 406 are located at a position corresponding to the focal length F of the lenslets 408. In the illustrative embodiment, the refractometer 400 includes the relay lenses 428 and 430. The relay lenses 428 and 430 are used to modify the working distance between the user's eye 420 and the refractometer 400. Skilled artisans will appreciate that other relay systems including mirrors (not shown) may be utilized without deviating from the spirit of the invention. The relay lenses 428 and 430 are positioned in the plane perpendicular to the axis Z of the refractometer 400. In the illustrative embodiment, the optical axes of the relay lenses 428 and 430 correspond to the axis Z. In another embodiment, the relay lenses 428 and 430 are located a suitable distance away from the lenslet array 408. In another embodiment, the distance L between the relay lenses 428 and 430 is fixed. In yet another embodiment, the relay lenses 428 and 430 are the substantially the same. In the illustrative embodiment, the distance L between the relay lenses 428 and 430 affects a characteristic of the optical signal being relayed.

The eye 420 will be described next. The perfect eye 420 receives light which is ideally focused onto the retina 412 through the cumulative convergence of the cornea 418, the lens 419, and the fluids 421 of the eye 420. Refractive errors in the eye 420 affect the point of focus of the light. For example, in nearsighted subjects, the point of focus falls short of the retina 412 allowing images close to the eye 420 to be relatively clearly viewed, while blurring distant images. Conversely, in farsighted subjects, the point of focus falls past the retina 412 allowing distant images to be relatively clearly viewed, while blurring images close to the eye 420. The eye 420 is located with respect to the refractometer 400 such that light exiting the relay lens 430 will impinge on the cornea 418 and be directed towards the retina 412. In one embodiment, the optic axis of the lens 419 corresponds to the Z-axis. In another embodiment, the optic axis of the lens 419 corresponds to the optic axes of the rely lenses 428 and 430. In a typical embodiment, the lens 419 is tilted with respect to the Z-axis. This lens 419 tilt can contribute to the aberrations of the eye 420. In another embodiment, the lens 419 is tilted with respect to the cornea 418.

One embodiment of the operation of refractometer 400 will be described next. In this embodiment, the spatial light pattern generator 402 is a spatial light modulator (SLM). The SLM 402 is an array of light sources, as previously discussed with reference to FIG. 2. A controller (not shown) switches on a single light source 404 from the SLM 402. Rays 405 from light source 404 impinge on lenslet 410. The distance between light source 404 and lenslet 410 is predetermined such that the beam 414 exiting lenslet 410 is substantially collimated. The collimated beam 414 is achieved when the rays of light from the beam are parallel to each other. Hence, the collimated beam 414 neither converges nor diverges until it encounters an element that modifies it. The collimation occurs at a distance F, the focal length of lenslet 410. In another embodiment, suitable collimation occurs at a distance in the vicinity of the focal length F of lenslet 410.

In one embodiment of the invention, the rays 405 from the light source 404 impinge on undesired lenslets 410' and 410" as well as a desired lenslet 410. A series of baffles (not shown) can be used to control the light from the light source 404. The baffles are placed between the lenslets 410, 410' and 410", to keep stray light from impinging on an improper lenslets 410' and 410". The baffles are not necessary in the illustrative embodiment.

Collimated beam 414 next encounters the relay lenses 428 and 430. In this embodiment, relay lenses are used to vary the working distance between the refractometer 400 and the user's eye 420. In the preferred embodiment, the relay lenses 428 and 430 receive the collimated light beam 414 and transmit an inverted but otherwise substantially the same collimated light beam 414'. In another embodiment, the relay lenses 428 and 430 have different focal lengths. In that embodiment, the collimated beam 414 has a different diameter than the collimated beam 414'. In another embodiment, pluralities of relay lens sets are used. In a further embodiment, suitable is optical mirrors (not shown) are used to relay the collimated beam 414 to a desired location. In yet another embodiment, a combination of relay lenses and mirrors is used. In still another embodiment, a relay mechanism is not required.

The collimated beam 414' next encounters the eye 420. The eye 420 includes a cornea 418, a lens 419 and fluid 421 which all contribute to focusing the collimated beam 414' onto the retina 412. In this embodiment, the collimated beam 414' is focused by the eye 420 to the point A 404' on the retina 412. The point A 404' on the retina 412 represents the light that has entered the eye 420 through a portion of the pupil 426 defined by the image of the lenslet 410. Next, the single light source 406 is switched on by a controller (not shown). The rays 407 impinge on the lenslet 410 from a different source location than the ray 405. The light source 406 is at a distance corresponding to the focal length F of the lenslet 410. The lenslet 410 generates collimated beam 416 corresponding to the light source 406. The collimated beam 416 encounters the relay lenses 428 and 430. The relay lenses 428 and 430 invert and relay the collimated beam 416 to generate the collimated beam 416'. The collimated beam 416' enters the pupil 426 at the same location as does the collimated beam 414'. The eye 420 focuses the collimated beam 416' to the point A' 406' on the retina 412. As different point sources from different locations on the spatial light pattern generator 402 are illuminated by a controller (not shown), the angle at which the light enters the eye 420 changes. This changes the position of the point A on the retina 412. In one embodiment, the spatial light pattern generator 402 is a spatial light modulator (SLM).

The aberrations in the system can be characterized by exploiting this technique. In one embodiment, each light source in the SLM 402 is sequentially switched on by a controller (not shown), and a corresponding location of that light source image is formed on the retina 412. Changing the position of the light source changes the angle at which the light enters the eye 420. The controller (not shown) sequentially switches on various light sources from the SLM 402 until one light source aligns with a reference location on the retina 412. The position of the reference light source corresponds to the angle in which the light was required to bend through the cornea to contact the reference location on the retina 412. By mapping the location of the light source versus the position of the image on the retina 412, the characteristics of the wavefront aberration of the eye 420 are observed, in one embodiment, by a processor (not shown). The controller (not shown) accomplishes this by making successive measurements across each lenslet 410 in the lenslet array 408. The measurements generate a set of light entry angles for the eye 420. An estimate of the wavefront aberration for the eye 420 is readily computed from the set of light entry angles.

Figure 5:
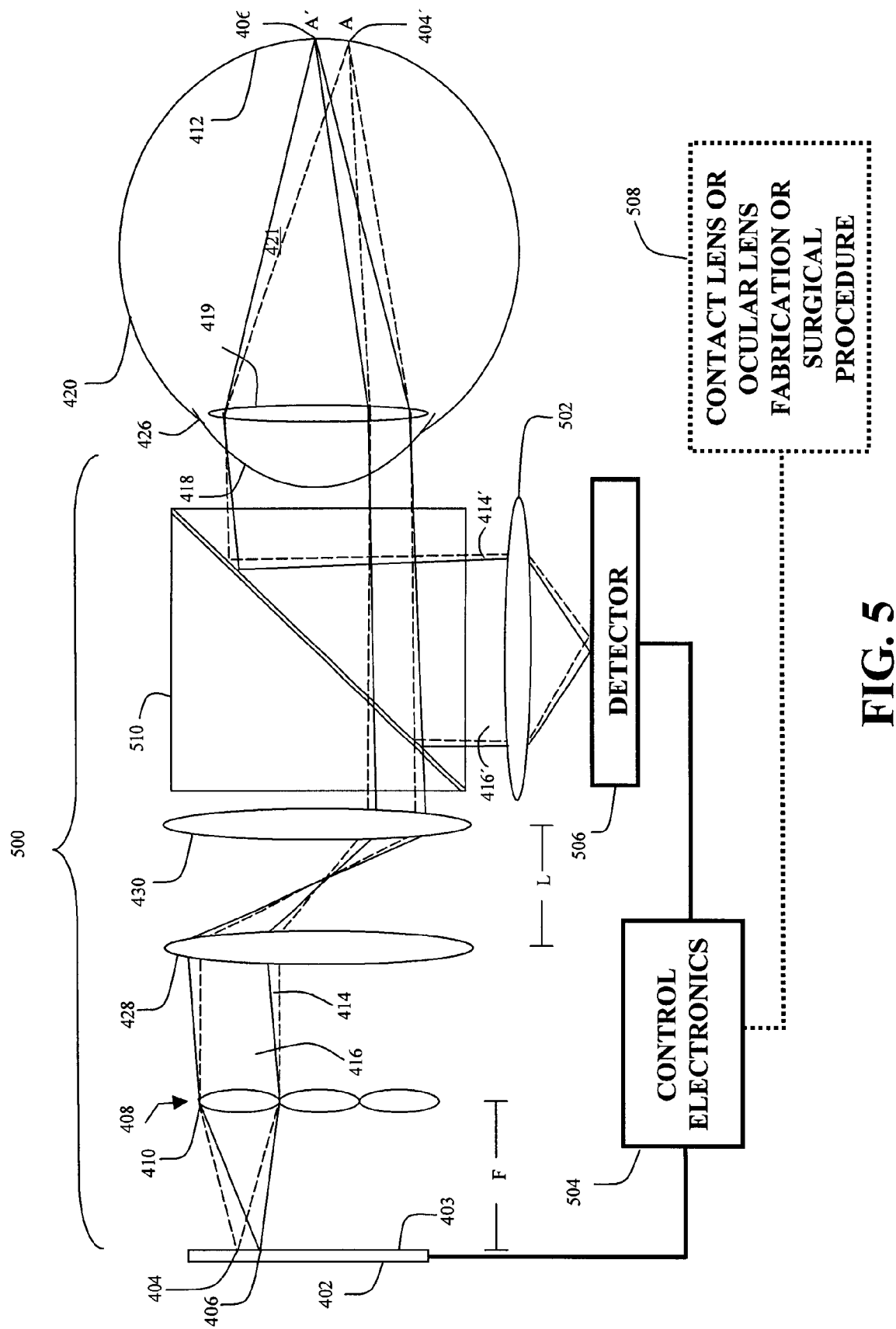
FIG. 5 is a schematic block diagram of an illustrative wavefront sensor for measuring characteristics of an eye according to another embodiment of the invention.

In the embodiment described above, the eye 420 of the user should be fixed on a referenced target, such as a bullseye or a reticle. This is to ensure that the light enters though a fixed portion of the pupil 426 of the eye 420. In an alternate embodiment, the light impinging on the retina 412 is imaged through another optical apparatus onto a spatially resolved measurement device, such as a camera or an array detector. In this embodiment, the displacement of the spot A 404' is measured as a function of the entry pupil position. FIG. 5 illustrates such an embodiment.

In an alternate embodiment, an operation of the refractometer 400 is described as follows. In this embodiment, the spatial light pattern generator 402 is a spatial light modulator (SLM). A controller (not shown) switches on a plurality of light sources 404 from the SLM 402. The plurality of light sources 404 form a predetermined pattern. Rays 405 from each light source 404 impinge on corresponding lenslets 410. The distance between each light source 404 and each lenslet 410 is predetermined such that each beam 414 exiting each lenslet 410 is substantially collimated.

Each collimated beam 414 in the pattern next encounters the relay lenses 428 and 430. In one preferred embodiment, the relay lenses 428 and 430 receive each collimated light beam 414 and transmit an inverted but otherwise substantially same collimated light beam 414.

Each collimated beam 414' in the pattern next encounters the eye 420. The eye 420 includes a cornea 418, a lens 419 and fluid 421 which all contribute to focusing each collimated beam 414' onto the retina 412. In this embodiment, each collimated beam 414' is focused by the eye 420 to points on the retina 412 (not shown). The points on the retina 412 represents the light that has entered the eye 420 through those portions of the pupil 426 defined by the images of the lenslets 410. The points on the retina correspond to the pattern from the SLM 402.

As different point sources from different locations on the SLM 402 are illuminated by a controller (not shown), the angle at which the light enters the eye 420 changes. This changes the position of the points A on the retina 412. The SLM 402 projects a pattern of points onto the retina 412. Using this technique, the aberrations in the system can be characterized. In one embodiment, a pattern of light sources in the SLM 402 is switched on by a controller (not shown), and corresponding locations of those light source images are formed on the retina 412. An estimate of the wavefront aberration for the eye 420 is made by measuring the displacement of each of the light source images in the pattern from their ideal locations. In one embodiment, a camera is used to photograph the pattern on the retina. Skilled artisans will appreciate that other devices could be used such as charge coupled device (CCD) cameras, photosensitive film, array detectors, or the like.

In another embodiment, a reference pattern is projected, and the displacement of a projected measurement pattern from the reference pattern is measured. In yet another embodiment, the reference pattern is moved while the measurement pattern is observed. In these embodiments, a visual rendering of the retina is used.

FIG. 5 is a schematic block diagram of an illustrative wavefront sensor 500 for measuring characteristics of an eye 420 according to another embodiment of the invention. The wavefront sensor 500 is also referred to as a refractometer. The front surface 403 of the spatial light pattern generator 402 contains the light modulating elements 404 and 406. That surface 403 is disposed in a plane perpendicular to axis Z of the refractometer 500. The lenslet array 408 comprises a plurality of evenly spaced lenslets 410 arranged in a planar configuration. In one embodiment, the lenslets 410 are arranged in a matrix configuration. In another embodiment, the lenslets 410 are arranged in a radial configuration. In yet another embodiment, the positions of the lenslets 410 with respect to one another is varied. The light modulating elements 404 and 406 are located at a position corresponding to the focal length F of the lenslets 408. In the illustrative embodiment, the refractometer 500 includes the relay lenses 428 and 430. The relay lenses 428 and 430 are used to modify the working distance between the user's eye 420 and the refractometer 500. Skilled artisans will appreciate that other relay systems including mirrors (not shown) may be utilized without deviating from the spirit of the invention. In one embodiment, the relay lenses 428 and 430 are located a suitable distance away from the lenslet array 408. In another embodiment, the distance L between the relay lenses 428 and 430 is fixed. In yet another embodiment, the relay lenses 428 and 430 are the substantially the same. In the illustrative embodiment, the distance L between the relay lenses 428 and 430 affects a characteristic of the optical signal being relayed.

The refractometer 500 also includes beamsplitter 510. The beamsplitter 510 passes the light rays from the rely lens 430 to the cornea 418. The eye 420 focuses these rays onto the retina 412 at points A' 406' and A 406. The lens 502 images the points A' 406' and A 406 onto the detector 506. The beamsplitter 510 redirects at least a portion of the reflected light from the retina 412 to the lens 502. The reflected light 414' and 416' corresponds to the points 404' and 406', respectively. In one embodiment, the detector 506 is an array detector. In another embodiment, the detector 506 is a camera. In another embodiment, the detector 506 is a quadrant detector. In yet another embodiment, the detector 506 is an array of individual detectors. In still another embodiment, the detector 506 is a retina from another eye (e.g., a doctor's eye). In yet another embodiment, the detector 506 is a light sensitive detector, such as a photodetector. In one embodiment, the detector 506 couples to the control electronics 504. In another embodiment, the control electronics 504 includes a computer. The computer analyzes data generated by the refractometer 500. In one embodiment, the SLM 402 also couples to the control electronics 504. The control electronics 504 controls the output of the SLM 402. The control electronics 504 processes spatial information about points 404' and 406' as detected by detector 506 with respect to points 404 and 406 from the SLM 402. Since the control electronics 504 controls the SLM 402, the control electronics 504 can precisely determine the relationship between the point sources 404 and 406 on the SLM 402 and the points 404' and 406' on the retina 412, respectively. In other embodiments, the control electronics 504 provides the relationship data to contact lens fabrication equipment, ocular lens fabrication equipment, or surgical procedures 508. The ocular lens fabrication equipment includes fabrication of intraocular lenses. The surgical procedures include laser eye surgery or any procedures which entail the shaping of the eye 420.

The operation of the refractometer 500 will be described next. As previously described, the spatial light pattern generator 402 is a spatial light modulator (SLM). The SLM 402 is an array of light sources. The control electronics 504 switches on a single light source 404 from SLM 402. Rays from the light source 404 impinge on the lenslet 410. The focal length F, of lenslet 410 determines the distance between the light source 404 and the lenslet 410 such that the beam exiting lenslet 410 is substantially collimated.

The collimated beam 414 next encounters the relay lenses 428 and 430. In this embodiment, the relay lenses 428 and 430 vary the working distance between the refractometer 500 and the user's eye 420. In one preferred embodiment, the relay lenses 428 and 430 receive the collimated light beam 414 and transmit an inverted but otherwise substantially the same collimated light beam. The relayed collimated beam 414 next encounters the beamsplitter 510. The beamsplitter 510 passes a portion of the relayed beam 414 to the eye 420. The cornea 418, the lens 419, and the fluid 421 of the eye 420 focus the relayed beam 414 onto the retina 412 at the point A 404'. The point A 404' on the retina 412 represents the light that has entered the eye 420 through a portion of the pupil defined by the image of the lenslet 410. The point 404' on the retina 412 acts as a virtual point source in the refractometer 500. The lens 502 images the point 404' onto the detector 506. The location of the point 404' on the detector 506 corresponds to the location of the point 404' on the retina 412. The detector 506 generates a signal having a spatial location. The control electronics 504 receives the signal from the detector 506.

Next, the control electronics 504 switches on the single light source 406. The rays from source 406 impinge on the lenslet 410 from a different source location than the rays from source 404. The light source 406 is at a distance corresponding to the focal length F of the lenslet 410. The lenslet 410 generates collimated beam 416 corresponding to the light source 406. The collimated beam 416 encounters relay lenses 428 and 430. The relay lenses 428 and 430 invert and relay the collimated beam 416. The eye 420 focuses the relayed beam 416 to the point A'406' on the retina 412. As different point sources from different locations on the SLM 402 are illuminated by the control electronics 504, the angle at which the light enters the eye 420 changes. This affects the position of the point of focus of that light on the retina 412. The point 406' on the retina 412 acts as a virtual point source in the refractometer 500. The lens 502 images the point 406' onto the detector 506. The location of the point 406' on the detector 506 corresponds to the location of point 406' on the retina 412. The detector 506 generates a signal having a spatial location. The control electronics 504 receives the signal from the detector 506.

By knowing the location of each point source on the SLM 402 and the location of each virtual point source on the detector 506, the control electronics 504 can calculate the location of each point source corresponding to an ideal eye 420. The control electronics 504 sends the location of each point source corresponding to the ideal eye 420 to a lens fabrication system 508. The lens fabrication system 508 uses the location data to generate a corrective lens. The corrective lens compensates for the optical aberrations of the eye 420. In another embodiment, the control electronics 504 sends the location data to a surgical system 508. The surgical system 508 uses the location data to reshape the eye 420. The reshaping of the eye 420 corrects for the optical aberrations detected by the refractometer 500. Hence, the aberrations of the eye 420 are characterized and corrected by exploiting this technique. In an alternate embodiment, the control electronics 504 sequentially switches on each light source in the SLM 402, and a corresponding location of that light source image is formed on the retina 412.

Figure 6:
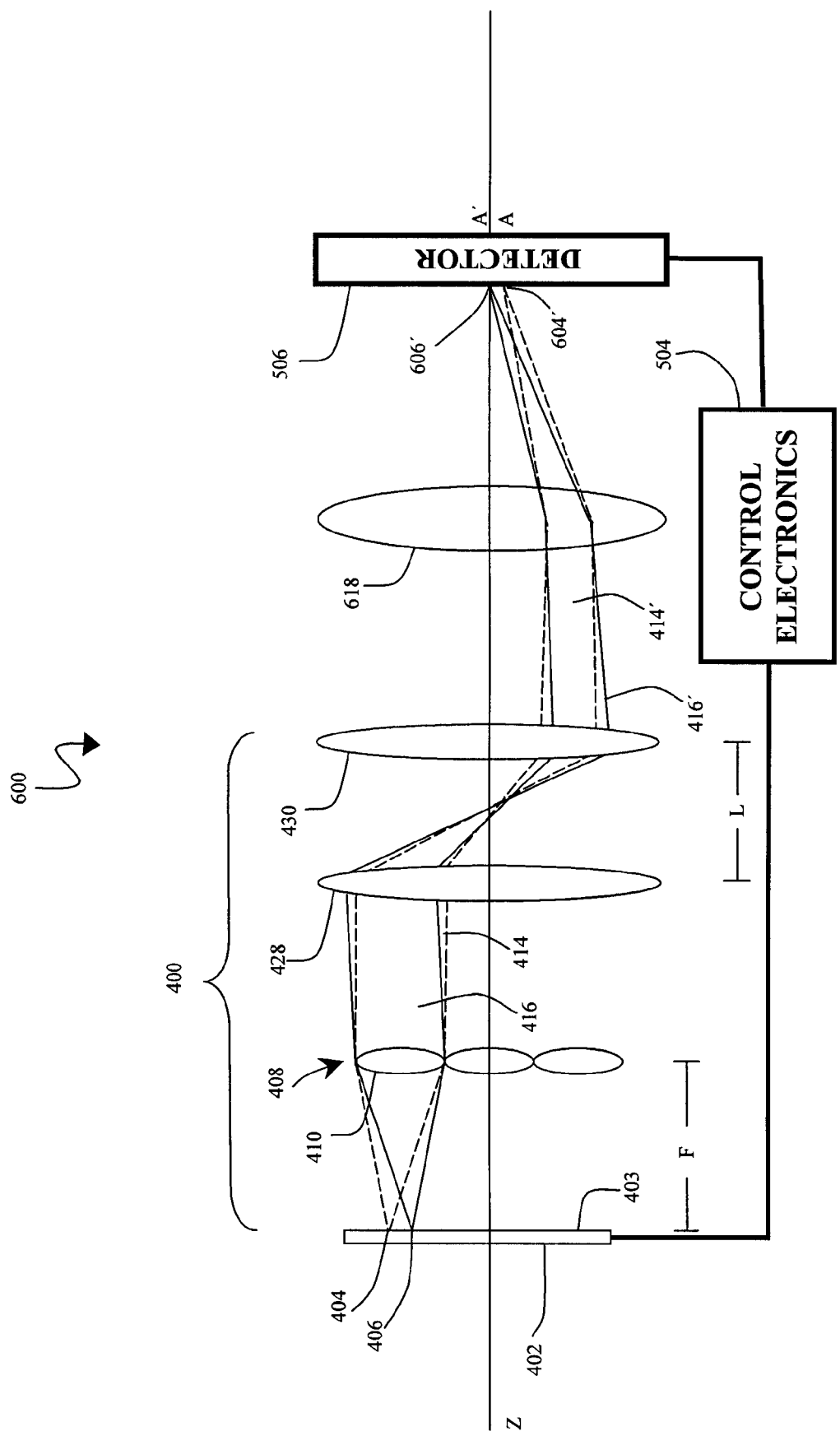
FIG. 6 is a schematic block diagram of an illustrative wavefront sensor for measuring characteristics of a lens according to one embodiment of the invention.

FIG. 6 is a block diagram of a wavefront sensor 600 for measuring the optical aberrations of a lens 618 according to an embodiment of the invention. The wavefront sensor 600, in other embodiments, is used to characterize the aberrations in optical elements (i.e., mirrors) and optical systems (i.e., telescopes). The front surface 403 of the spatial light pattern generator 402 contains the light modulating elements 404 and 406. The light modulating elements 404 and 406 are located at a position corresponding to the focal length F of the lenslets 408. In the illustrative embodiment, the wavefront sensor 600 includes the relay lenses 428 and 430. The relay lenses 428 and 430 modify the working distance between the user's eye 420 and the refractometer 400. Skilled artisans will appreciate that other relay systems including mirrors (not shown) may be utilized without deviating from the spirit of the invention. In another embodiment, relay lenses 428 and 430 are not used at all (not shown). In yet another embodiment, a system designer locates the relay lenses 428 and 430 a suitable distance away from the lenslet array 408.

The lens 618 will be described next. The perfect lens 618 receives light which is ideally focused onto a single point on the detector 506. Refractive errors in the lens 618 affect the point of focus of the light. The lens 618 is located with respect to the refractometer 400 such that light exiting relay lens 430 will impinge on the lens 618 and be focused onto a point on the detector 506. In one embodiment, the detector 506 is an array detector. In another embodiment, the detector 506 is a camera. In yet another embodiment, the detector 506 is a quadrant detector. In yet another embodiment, the detector 506 is an array of individual detectors. In yet another embodiment, the detector 506 is a light sensitive detector, such as a photodetector or a photodiode.

In one embodiment, the detector 506 couples to the control electronics 504. The control electronics 504 includes a computer. The control electronics 504 receives data from the detector 506. The data corresponds to the locations 604' and 606' on the detector 506. The aberrations of lens 618 are determined by repeating this technique across the surface of lens 618. The control electronics 504 compares location data from the spatial pattern generator 402 with location data form the detector 506. The control electronics 504 uses the data to generate wavefront data. The wavefront data is a measure of the aberrations of lens 618. In another embodiment, a mirror (not shown) replaces the lens 618. In other embodiments, the mirror is a spherical mirror, a concave mirror, a convex mirror, an elliptical mirror, a planar mirror, a flexible mirror, or the like.

In yet another embodiment, the mirror is a segmented mirror for use with an adaptive optics system. One type of adaptive optics system is used to compensate for atmospheric effects on large telescopes such as temperature variations. In one embodiment, the large telescope uses a large mirror comprised of segmented portions. Each mirror portion couples to an actuator which controls the location of the mirror portion. The actuators couple to a processor. The processor determines the ideal position of each mirror portion and adjusts the actuators accordingly. In this embodiment, the refractometer 400 is used to adjust the mirror portions to "null" the aberrations of the segmented mirror. The control electronics 504 acquires knowledge of the ideal location of each mirror portion in the segmented mirror through the use of the refractometer 400 and the detector 506.

One object of the wavefront sensor 600 is to measure the deviations of the wavefront surface from a plane. In the case of a telescope, for example, small temperature variations in the earth's atmosphere cause the light entering different parts of the telescope pupil to travel at slightly different speed, producing variations in the optical path. These variations in the optical path cause images of astronomical objects to become blurred. By measuring these path length differences across the telescope pupil, an adaptive optics system (such as that of FIG. 7) can correct them in real time using a segmented mirrors having a plurality of mirror portions or a flexible mirror. The adaptive optics system 700 sharpens the astronomical images. Since the atmosphere is constantly shifting, the adaptive optics system constantly adjusts to those shifts. The wavefront sensor 600 monitors these atmospheric shifts. In another embodiment, the wavefront sensor 600 inputs compensation values into the adaptive optics system 700.

The operation of the wavefront sensor 600 will be described next. In one embodiment, the spatial light pattern generator 402 is a spatial light modulator (SLM). A single light source 404 from SLM 402 is switched on. Rays from the light source 404 impinge on the lenslet 410. The distance between the light source 404 and the lenslet 410 is predetermined such that the beam 414 exiting the lenslet 410 is substantially collimated. This collimation occurs at a distance F, the focal length of the lenslet 410.

The collimated beam 414 next encounters the relay lenses 428 and 430. In this embodiment, relay lenses vary the working distance between the refractometer 400 and the lens 618. In one preferred embodiment, the relay lenses 428 and 430 receive the collimated light beam 414 and transmit an inverted but otherwise substantially the same collimated light beam 414'. In another embodiment, the relay lenses 428 and 430 have different focal lengths. In that embodiment, the collimated beam 414 has a different diameter than the collimated beam 414'. Another embodiment employs pluralities of relay lens sets. A further embodiment employs suitable optical mirrors (not shown) to relay the collimated beam 414 to a desired location. Yet another embodiment utilizes a combination of relay lenses and mirrors.

The collimated beam 414' next encounters the lens 618. The lens 618 modifies an optical signal as it traverses the lens 618. In the embodiment shown, the lens 618 is a focusing lens. In another embodiment the lens 618 is a diverging lens (not shown). In still other embodiments, a mirror (not shown) replaces the lens 618. In yet another embodiment, a multiple element optical system (not shown) replaces the lens 618. The point A 604' on the detector 506 represents the light that has entered the lens 618 through a portion of the lens 618 defined by the image of the lenslet 410. Next, the point source 406 is switched on. The rays from that point source impinge on the lenslet 410 from a different source location than the rays from the point source 404.

The point source 406 is at a distance corresponding to the focal length F of the lenslet 410. The lenslet 410 generates the collimated beam 416 corresponding to the light source 406. The collimated beam 416 encounters the relay lenses 428 and 430. The relay lenses 428 and 430 invert and relay the collimated beam 416 to generate the collimated beam 416'. The collimated beam 416' enters the lens 618 at the same location as the collimated beam 414'. The lens 618 focuses the collimated beam 416' to the point A' 406' on the detector 506. As the control electronics 504 switches on different point sources from different locations on the SLM 402, the angle at which the light enters the lens changes corresponding to the locations of the illuminated point sources. These angles change the position of the point A on the detector 506.

The aberrations in the system can be characterized by exploiting this technique. In one embodiment, the control electronics 504 sequentially switches on each light source in the SLM 402, which forms an image at a corresponding location of that light source on the detector 506. Changing the position of the light source changes the angle at which the light enters the lens 618. The control electronics 504 sequentially switches on various light sources from the SLM 402 until one light source aligns with a reference location on the detector 506. The position of that light source corresponds to the angle in which the light was required to bend through the lens 618 to contact the reference location on the detector 506. By mapping the location of the light source versus the position of the image on the detector 506, the characteristics of the wavefront aberration of the lens 618 are realized. This is accomplished by making successive measurements across each lenslet 410 in the lenslet array 408. The measurements generate a set of light entry angles for the lens 618. An estimate of the wavefront aberration for the lens 618 is readily computed by the control electronics 504 from the set of light entry angles. In one embodiment, the control electronics 504 includes a computer or a processor.

Figure 7:
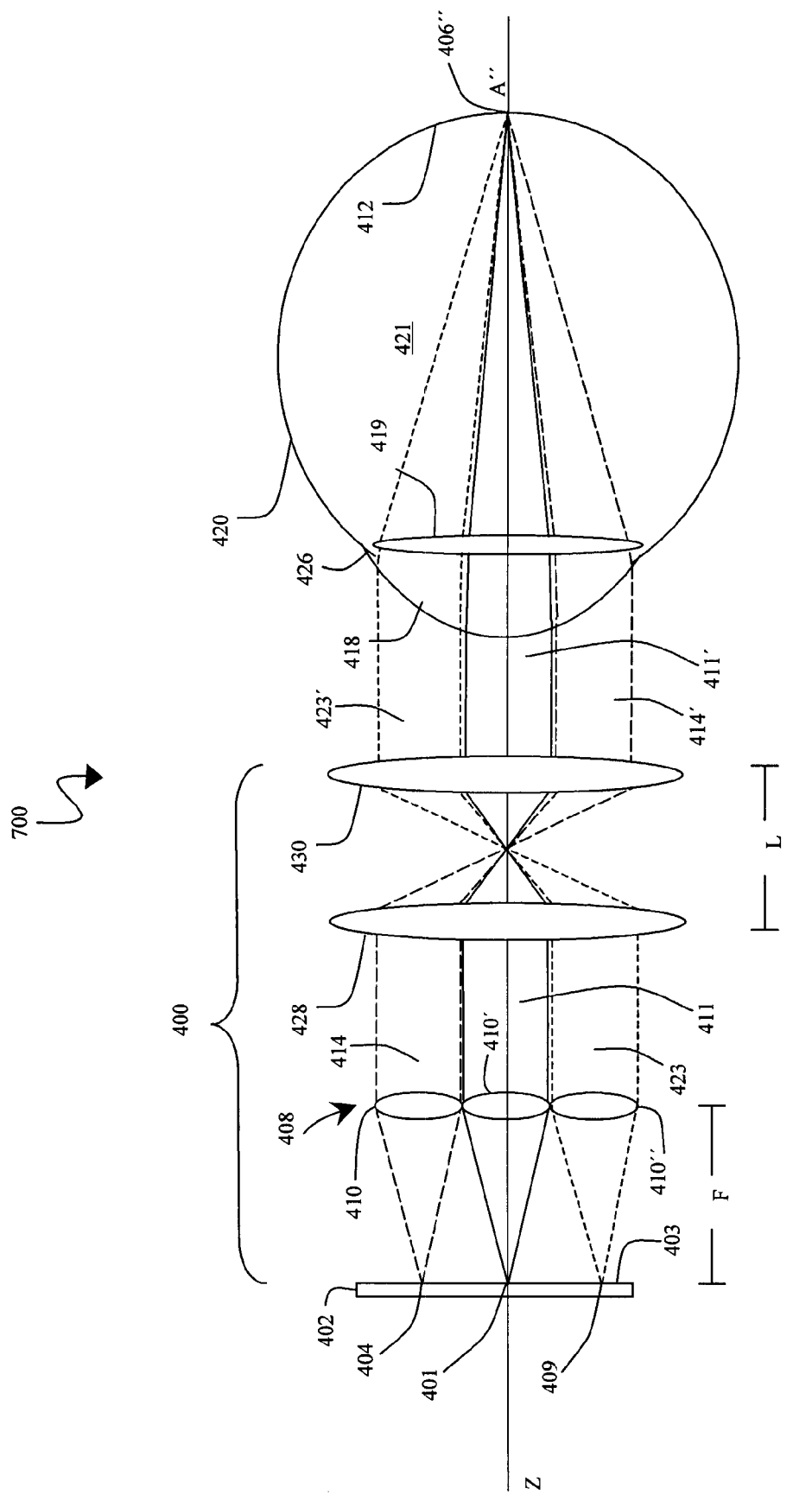
FIG. 7 is a schematic block diagram of an illustrative adaptive optics system for projecting a diffraction limited image according to an embodiment of the invention.

FIG. 7 shows one illustrative achievement of the invention. FIG. 7 illustrates an adaptive optics system 700 for projecting a diffraction limited image 406" according to one embodiment of the invention. In the embodiment shown, the system 700 projects a diffraction limited image 406" on the retina 412 of the eye 420. In other embodiments, the system 700 projects a diffraction limited image 406" onto a detector, a camera, a charge coupled device (CCD) detector, or the like. In other embodiments, a lens, a mirror, or other optical element replaces the eye 420. Skilled artisans will appreciate the myriad of uses for the adaptive optics system 700 of the present invention, including, for example, compensating for atmospheric effects in telescopes.

The adaptive optics system 700 utilizes the same components from the refractometer 400 in a different manner. The front surface 403 of the spatial light pattern generator 402 contains the light modulating elements 404, 401 and 409. In one embodiment, the surface 403 can be disposed in a plane perpendicular to axis Z of the refractometer 400. The lenslet array 408 comprises a plurality of evenly spaced lenslets 410, 410' and 410" arranged in a planar configuration. In another embodiment, the lenslet array 408 can be disposed in the plane perpendicular to axis Z of the refractometer 400. The system designer locates the light modulating elements 404, 401 and 409 at a position corresponding to the focal length F of the lenslets 408. In the illustrative embodiment, the refractometer 400 includes the relay lenses 428 and 430. The relay lenses 428 and 430 modify the working distance between the user's eye 420 and the refractometer 400. Skilled artisans will appreciate that other relay systems including mirrors (not shown) may be utilized without deviating from the spirit of the invention. The system designer positions the relay lenses 428 and 430 in the plane perpendicular to the Z-axis of the refractometer 400. In the illustrative embodiment, the optical axes of the relay lenses 428 and 430 correspond to the Z-axis. In another embodiment, the system designer locates the relay lenses 428 and 430 a suitable distance away from the lenslet array 408.

The operation of adaptive optics system 700 will be described next. In one embodiment, the spatial light pattern generator 402 is a spatial light modulator (SLM). In another embodiment, the spatial light pattern generator 402 comprises a plurality of coherently related point sources arranged in an array configuration. In yet another embodiment, the spatial light pattern generator 402 comprises a uniform light source 232 of the configuration shown in FIG. 2F.

The refractometer 400 operates in the same manner as described with reference to FIG. 4. The refractometer 400 determines the locations of the point sources 404, 401, and 409 on the spatial light pattern generator 402 corresponding to the wavefront aberrations of the eye 420. A suitable number of point sources from the spatial light pattern generator 402 are illuminated by a controller (not shown) based on the desired resolution. Once the refractometer 400 determines the proper spatial locations of the point sources from the spatial light pattern generator 402, the adaptive optics system 700 utilizes the location data. As an illustrative example, the controller (not shown) illuminates the point sources 404, 401, and 409 on the spatial light pattern generator 402 in sites corresponding to a wavefront aberration compensated eye 420. When illuminated, the light from each point source 404, 401, and 409 focuses on the same spot 406" on the retina 412. In one embodiment, the point sources 404, 401, and 409 are coherent with respect to one another.

The controller illuminates a single light source 404 from the spatial light pattern generator 402. Rays from point source 404 impinge on lenslet 410. The distance between point source 404 and lenslet 410 corresponds to the focal length F of the lenslet 410 such that the beam 414 exiting lenslet 410 is substantially collimated. The collimated beam 414 next encounters relay lenses 428 and 430. In one preferred embodiment, the relay lenses 428 and 430 receive the collimated light beam 414 and transmit an inverted but otherwise substantially the same collimated light beam 414'. The collimated beam 414' next encounters the eye 420. In the illustrative embodiment, the eye 420 focuses the collimated beam 414' to the point 406 on the retina 412. The point 406" on the retina 412 represents the light that has entered the eye 420 through a portion of the pupil defined by the image of the lenslet 410. Since the point source 404 is at a location corresponding to the compensated wavefront, the eye 420 focuses the collimated beam 423' to the point 406" on the retina 412.

Next, the controller switches on a single light source 401 from spatial light pattern generator 402. Rays from point source 401 impinge on lenslet 410'. The distance between point source 401 and lenslet 410' is predetermined such that the beam 411 exiting lenslet 410 is substantially collimated. Collimated beam 411 next encounters the relay lenses 428 and 430. In the preferred embodiment, relay lenses 428 and 430 receive the collimated light beam 411 and transmit an inverted but otherwise substantially the same collimated light beam 411'. The collimated beam 411' next encounters the eye 420. In the illustrative embodiment, the eye 420 focuses the collimated beam 411' to the point 406" on the retina 412. The point 406" on the retina 412 represents the light that has entered the eye 420 through a portion of the pupil defined by the image of the lenslet 410'. Since the point source 401 is at a location corresponding to the compensated wavefront, the eye 420 focuses the collimated beam 411' to the point 406" on the retina 412.

Next, the controller switches on another single light source 409 from spatial light pattern generator 402. Rays from point source 409 impinge on lenslet 410". The distance between point source 409 and lenslet 410" is predetermined such that the beam 419 exiting lenslet 410" is substantially collimated. Collimated beam 419 next encounters relay lenses 428 and 430. In the preferred embodiment, relay lenses 428 and 430 receive the collimated light beam 419 and transmit an inverted but otherwise substantially the same collimated light beam 419'. The collimated beam 419' next encounters the eye 420. In the illustrative embodiment, the eye 420 focuses the collimated beam 419' to the point 406" on the retina 412. The point 406 on the retina 412 represents the light that has entered the eye 420 through a portion of the pupil defined by the image of the lenslet 410". Since the point source 409 is at a location corresponding to the compensated wavefront, the eye 420 focuses the collimated beam 419' to the point 406" on the retina 412.

Once a set of compensated point sources on the spatial light pattern generator 402 is defined, each point source is precisely imaged at a point 406" on the retina 412. By switching on all of the compensated point sources at once, the resultant image on the retina depends on the coherence relationship between the points. If the point sources are incoherently related, then the image on the retina 412 is a superposition of blurred circles corresponding to each of the lenslets 410 in the lenslet array 408. If the point sources are coherently related, that is, if each point source emits light of the same wavelength and phase, the points imaged on the retina 412 add coherently. In that case, the spot size on the retina is equivalent to the spot size of the entire pupil of the eye 420. Hence, a diffraction limited spot for the entire pupil is realized.

In one embodiment, emission of coherent light is achieved through the use of programmable actuated mirrors. Illuminating the mirrors with a laser and selecting the appropriate mirrors to actuate generates a spatial light pattern. Each point in the spatial light pattern emits light of the same wavelength and phase.

In one embodiment, the adaptive optics system 700 of the invention compensates for the aberrations in a lens, such as a telescope objective. In another embodiment, the adaptive optics system compensates for the aberrations in a multiple element optical component. In yet another embodiment, the adaptive optics system 700 compensates for the aberrations in a mirror.

One contemplated use for the adaptive optics system 700 is by optometrists or eye surgeons. Eye surgeons can use the adaptive optics system 700 to illustrate the expected post-surgery improvement in a patient's vision. This "try before you buy" system 700 enables patients to decide whether the improvement in their vision is worth undergoing the surgery. The operation of the system 700 is as follows. A patient considering eye surgery for vision improvement looks into an eye input port (not shown) in the system 700. The system 700 reveals an image to the patient. Selecting specific point sources on the spatial light pattern generator 402 forms a diffraction limited spot on the retina 420. The system then scans the diffraction limited spot across the pupil 426 of the eye 420 creating the image viewed by the patient. If the patient's eye 420 is imperfect, the patient sees an image which is blurred. The system 700 then performs a series of measurements across the surface of the eye 420 to determine the wavefront aberrations of the eye 420. The system 700 uses that data to determine which point sources on the spatial light pattern generator 402 are required to bring the image into focus for the eye 420. The controller illuminates those point sources, and the patient sees an improvement in the focus of the image. If the improvement is not adequate, the patient can decide to forego the surgery. By compensating for the wavefront aberrations of the eye, the system 700 precisely models the result of a laser reshaping the eye. In some cases, reshaping of the eye through the use of a laser or other means does not result in sufficient vision improvement. In those cases, the system 700 spares the patient the risk, time, expense, pain, and recovery of the surgery.

In another embodiment, the adaptive optics system 700 generates a single, diffraction limited spot on the retina 412. In another embodiment, the adaptive optics system 700 generates a single, diffraction limited spot on an image plane or a detector (not shown). In yet another embodiment, the adaptive optics system 700 generates a high-resolution image of the retina 412. The high-resolution image is achieved, in one embodiment, by using the scanning system illustrated in FIG. 8.

Figure 8:
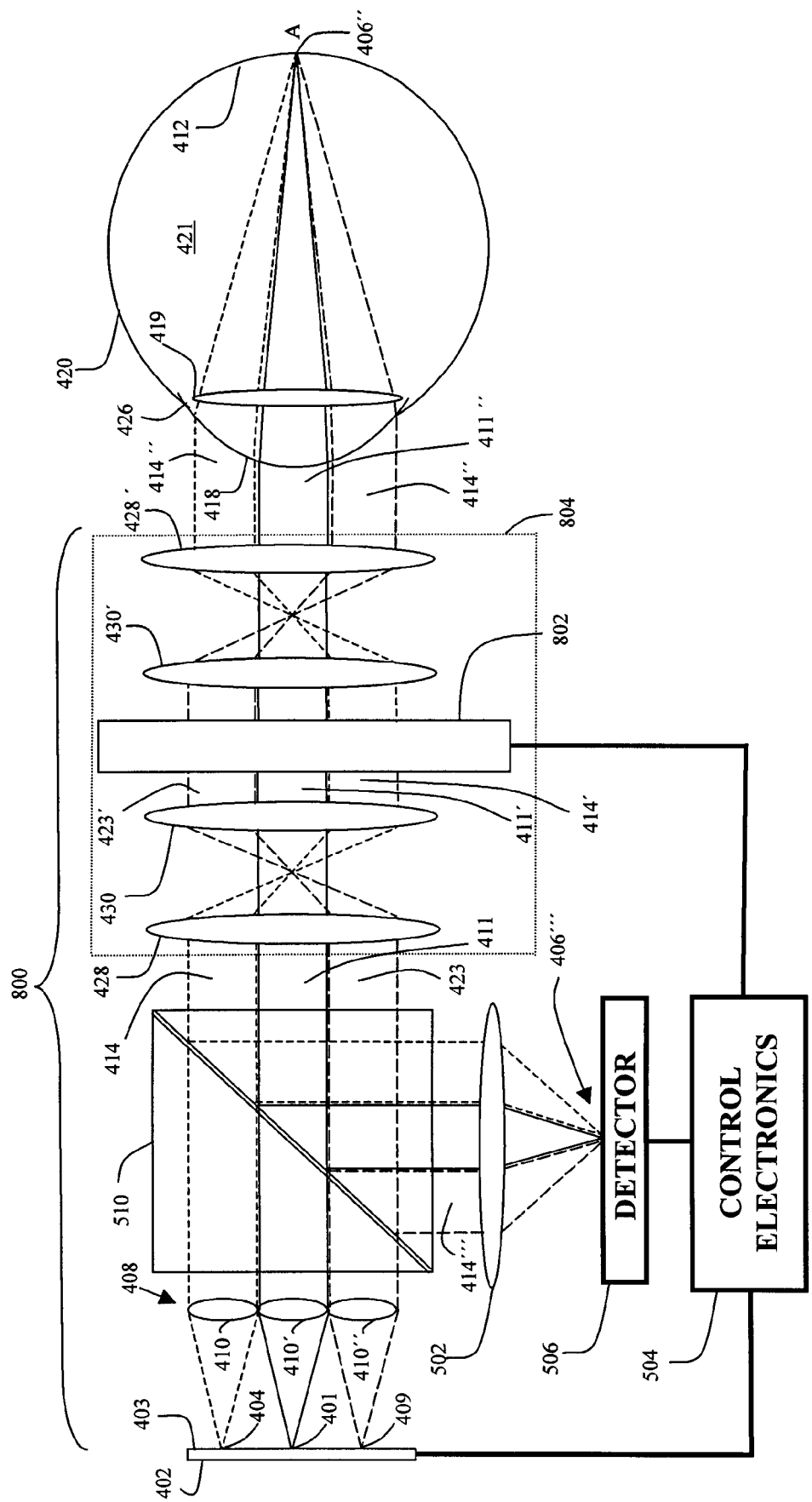
FIG. 8 is a schematic block diagram of an illustrative retinal scan system for obtaining a high-resolution image of the retina according to an embodiment of the invention.

FIG. 8 illustrates a retinal scan system for obtaining a high-resolution image of the retina according to an embodiment of the invention. The scan system of FIG. 8 uses concepts described with respect to the adaptive optics system of FIG. 7. FIG. 8 includes components described in FIG.

7 as well as a scanning device 802. The scanning device 802 is used to move the diffraction limited spot 406" across the pupil 426 to create the high resolution image of the retina 412. In one illustrative embodiment, a scanning device 804 includes the relay lenses 428, 430, 430' and 428'. In other embodiments, the scanning device 804 includes other relay mechanisms and optical components (not shown). Skilled artisans will appreciate that scanning devices suitable for use with the invention are commonly available. In one embodiment, the system 800 projects the diffraction limited image 406" onto the retina 412 of the eye 420. In other embodiments, the system 800 projects the diffraction limited image 406" onto a detector, a camera, a charge coupled device (CCD), or the like.

The components of FIG. 8 will be described next. The front surface 403 of the spatial light pattern generator 402 contains the light modulating elements 404, 401 and 409. The lenslet array 408 comprises a plurality of evenly spaced lenslets 410, 410' and 410" arranged in a planar configuration. The light modulating elements 404, 401 and 409 are disposed at a location corresponding to the focal length F of the lenslet array 408. In the illustrative embodiment, the system further includes the relay lenses 428 and 430, a scanning device 802, and the relay lenses 430' and 428'. The relay lenses 428, 430, 430' and 428' modify the working distance between the user's eye 420 and the system 800. Skilled artisans will appreciate that other relay systems including mirrors (not shown) may be utilized without deviating from the spirit of the invention. It will also be appreciated by skilled artisans that the system 800 can include both sets of relay lenses, one set of relay lenses, or no relay lenses at all. In one embodiment, the relay lenses are integrated as part of the scanning device 804. In one embodiment, the system 800 also includes a beamsplitter 510 and a detector 506. In another embodiment (not shown), the beamsplitter 510 is located to the right of the spatial pattern generator 402 in the system 800. This embodiment ensures that the detector receives aberration-compensated rays that travel back through the system 800 from the retina 412. In other embodiments, the detector 506 is a quadrant detector, a charge coupled device (CCD) detector, a camera, photosensitive film, or the like. In another embodiment, the system 800 also includes control electronics 504. In yet another embodiment, the control electronics 504 includes a computer.

The operation of adaptive scan system 800 will be described next. In one embodiment, the spatial light pattern generator 402 is a spatial light modulator (SLM). In another embodiment, the spatial light pattern generator 402 comprises a plurality of coherently related point sources arranged in an array configuration. In yet another embodiment, the spatial light pattern generator 402 comprises a uniform light source 232 of the configuration shown in FIG. 2F. In one embodiment, the uniform light source 232 is a laser.

The system 800 determines the locations of the point sources 404, 401, and 409 on the spatial light pattern generator 402 corresponding to the wavefront aberrations of the eye 420. A suitable number of point sources from the spatial light pattern generator 402 are illuminated based on the desired resolution. Once the system 800 determines the proper spatial locations of the point sources from the spatial light pattern generator 402, the system 800 utilizes the location data. As an illustrative example, the point sources 404, 401, and 409 are positioned on the spatial light pattern generator 402 in sites corresponding to a wavefront aberration compensated eye 420. When illuminated, the light from each point source 404, 401, and 409 focuses on the same spot 406" on the retina 412. The point sources 404, 401, and 409 are coherent with respect to one another.

The control electronics 504 illuminates a single light source 404 from the spatial light pattern generator 402. Rays from point source 404 impinge on lenslet 410. The distance between point source 404 and lenslet 410 is such that the beam 414 exiting lenslet 410 is substantially collimated. The collimated beam 414 next encounters relay lenses 428 and 430. In one preferred embodiment, the relay lenses 428 and 430 receive the collimated light beam 414 and transmit an inverted but otherwise substantially the same collimated light beam 414'. The collimated beam 414' next encounters the scanning device 802. In one embodiment, the scanning device 802 comprises a movable mirror for directing the collimated beam 414' to different locations across the pupil 426. Skilled artisans will appreciate that other embodiments of scanning devices 802, such as a galvanometer, can be used. In the illustrative embodiment, the collimated beam 414' next encounters relay lenses 430' and 428'. In one preferred embodiment, the relay lenses 430' and 428' receive the collimated light beam 414' and transmit an inverted but otherwise substantially the same collimated light beam 414". The collimated light beam 414" next encounters the eye 420. The eye 420 focuses the collimated beam 414' to the point 406" on the retina 412. The point 406" on the retina 412 represents the light that has entered the eye 420 through a portion of the pupil defmed by the image of the lenslet 410. Since the point source 404 is at a location corresponding to the compensated wavefront, the eye 420 focuses the collimated beam 414' to the point 406" on the retina 412.

Next, the control electronics 506 switches on a single light source 401 from the spatial light pattern generator 402. Rays from point source 401 impinge on lenslet 410'. The distance between point source 401 and lenslet 410' is the focal length F of lenslet 410'. Hence, beam 411 exiting lenslet 410 is substantially collimated. Collimated beam 411 next encounters the relay lenses 428 and 430. In the preferred embodiment, relay lenses 428 and 430 receive the collimated light beam 411 and transmit an inverted but otherwise substantially the same collimated light beam 411'. The collimated beam 411' next encounters the scanning device 802. The scanning device 802 transmits the collimated beam 411' to the relay lenses 430' and 428'. Relay lenses 430' and 428' transmit an inverted but otherwise substantially the same collimated beam 411". The collimated beam 411" next encounters the eye 420. In the illustrative embodiment, the eye 420 focuses the collimated beam 411" to the point 406" on the retina 412. The point 406" on the retina 412 represents the light that has entered the eye 420 through a portion of the pupil defined by the image of the lenslet 410'. Since the point source 401 is at a location corresponding to the compensated wavefront, the eye 420 focuses the collimated beam 411' to the point 406" on the retina 412.

Next, the control electronics 506 switches on another single light source 409 from the spatial light pattern generator 402. Rays from point source 409 impinge on lenslet 410. The distance between point source 409 and lenslet 410" is the focal length F of lenslet 410". Hence, beam 423 exiting lenslet 410" is substantially collimated. Collimated beam 423 next encounters the relay lenses 428 and 430. In the preferred embodiment, relay lenses 428 and 430 receive the collimated light beam 423 and transmit an inverted but otherwise substantially the same collimated light beam 423'. The collimated beam 423' next encounters the scanning device 802. The scanning device 802 transmits the collimated beam 423' to the relay lenses 430' and 428'. Relay lenses 430' and 428' transmit an inverted but otherwise substantially the same collimated beam 423". The collimated beam 423" next encounters the eye 420. In the illustrative embodiment, the eye 420 focuses the collimated beam 423 to the point 406" on the retina 412. The point 406" on the retina 412 represents the light that has entered the eye 420 through a its portion of the pupil defined by the image of the lenslet 410". Since the point source 401 is at a location corresponding to the compensated wavefront, the eye 420 focuses the collimated beam 423" to the point 406" on the retina 412.

Once a set of compensated point sources on the spatial light pattern generator 402 is defined, each point source is precisely imaged at a point 406" on the retina 412. When the control electronics 504 switches on all of the compensated point sources at once, the resultant image on the retina depends on the coherence relationship between the points. If the point sources are incoherently related, then the image on the retina 412 is a superposition of blurred circles corresponding to each of the lenslets 410 in the lenslet array 408. If the point sources are coherently related, that is, if each point source emits light of the same wavelength and phase, the points imaged on the retina 412 add coherently. In that case, the spot size on the retina is equivalent to the spot size of the entire pupil of the eye 420. Hence, a diffraction limited spot for the entire pupil is realized.

The point 406" on the retina 412 generated by point sources 404, 401, and 409 acts as a virtual point source to detector 506. In one embodiment, rays from the virtual point source 406" traverse the system 800 and impinge on detector 506 as a point 406'". In one embodiment, the virtual point source 406" traverses the pupil 426 of the imperfect eye 420. The aberrations of the eye 420 cause the detected point 406'" to blur on the detector 506. In another embodiment, the system 800 includes additional components (not shown) which compensate for the blur on the detector 506.

In one embodiment, emission of coherent light from the spatial light pattern generator 402 is achieved through the use of programmable actuated mirrors. Illuminating the mirrors with a laser and selecting the appropriate mirrors to actuate generates a spatial light pattern. In this embodiment, each point in the spatial light pattern emits light of the same wavelength and phase. Skilled artisans will appreciate the myriad of methods available to generate coherent light having a defined spatial pattern.

Once the system 800 generates the point 406 on the retina 412, that point generates collimated beams 414'", 411'" and 423'". Beamsplitter 510 redirects collimated beams 414'", 411'" and 423'" to lens 502. Lens 502 focuses beams 414'", 411'". and 423'" onto detector 506 as point 406'".

The control electronics 504 controls the scanning device 802. In one embodiment, the scanning device 802 performs a raster scan causing the point 406" to move across the retina 412. As the point 406" moves across the retina, the corresponding point 406'" moves across the surface of the detector 506. By choosing a sufficient number of scanned points a high-resolution image of the retina 412 can be realized.

In one embodiment, the control electronics 504 includes a computer. The computer controls the spatial light pattern generator 402, the detector 506, and the scanning device 802. In another embodiment, the computer generates a high-resolution image of the retina 412 based on the detected points 406'". In another embodiment, the patient observes an aberration compensated image generated by the scanned points 406". The aberration compensated image corresponds to the image a patient can expect post-surgery. The system 800 enables patients to decide whether the improvement in their vision is worth undergoing the surgery.

The operation of the system 800 is as follows. A patient considering eye surgery for vision improvement looks into an eye input port (not shown) in the system 800. The system 800 reveals an image to the patient. Selecting specific point sources on the spatial light pattern generator 402, and scanning those points across the pupil 426 forms an image on the retina 420. If the patient's eye 420 is imperfect, the patient sees an image which is blurred. The system 800 then performs a series of measurements across the surface of the eye 420 to determine the wavefront aberrations of the eye 420. The system 800 uses that data to determine which point sources on the spatial light pattern generator 402 are required to bring the image into focus for the eye 420. The control electronics 504 illuminated those compensated point sources, and the patient sees an improvement in the focus of the image. If the improvement is not adequate, the patient can decide to forego the surgery. By compensating for the wavefront aberrations of the eye, the system 800 precisely models the result of a laser reshaping the eye. In some cases, reshaping of the eye through the use of a laser or other means does not result in sufficient vision improvement. In those cases, the system 800 spares the patient the risk, time, expense, pain, and recovery of the surgery.

Having described and shown the preferred embodiments of the invention, it will now become apparent to one of skill in the art that other embodiments incorporating the concepts may be used and that many variations are possible which will still be within the scope and spirit of the claimed invention. It is felt, therefore, that these embodiments should not be limited to disclosed embodiments but rather should be limited only by the spirit and scope of the following claims.

What is claimed as new and secured by Letters Patent is:

1. An apparatus for determining a characteristic of an optical element, said apparatus comprising,
    a spatial light pattern generator adapted to generate at least one beam of light at a predetermined spatial position,
    at least one lenslet disposed in an array of lenslets adapted to receive said at least one beam of light from said spatial light pattern generator, and to direct said at least one beam of light to said optical element,
    a detector positioned to receive said beam of light subsequent to said beam of light encountering said optical element, and adapted to detect a received spatial position at which said detector receives said beam of light, and
    a processor adapted to compare said predetermined spatial position with said received spatial position to determine said characteristic of said optical element.

2. The apparatus of claim 1, wherein said processor is further adapted to change said is predetermined spatial position in response to said received spatial position.

3. The apparatus of claim 1, wherein said spatial light pattern generator comprises an opaque mask having a movable aperture.

4. The apparatus of claim 1, wherein said spatial light pattern generator comprises a spatial light modulator.

5. The apparatus of claim 1, wherein said spatial light pattern generator comprises an array of light emitting elements.

6. The apparatus of claim 5, wherein said light emitting elements are chosen from the group comprising light emitting diodes (LEDs), lasers, laserdiodes, and lamps.

7. The apparatus of claim 1, wherein said spatial light pattern generator comprises a cathode ray tube (CRT).

8. The apparatus of claim 1, wherein said spatial light pattern generator comprises a liquid crystal display (LCD).

9. The apparatus of claim 1, wherein said spatial light pattern generator comprises an array of individually addressable light-modulating elements.

10. The apparatus of claim 9 further comprising a uniform light source.

11. The apparatus of claim 9, wherein said uniform light source is a laser.

12. The apparatus of claim 1, wherein said lenslet is a microlens.

13. The apparatus of claim 1, wherein said array of lenslets is arranged in a substantially uniform pattern.

14. The apparatus of claim 13, wherein said substantially uniform pattern is chosen from the group comprising substantially a square, a triangle, a circle, a rectangle, an ellipse, a pentagon, a hexagon, an octagon, and substantially concentric circles.

15. The apparatus of claim 13, wherein said substantially uniform pattern comprises variably placed lenslets.

16. The apparatus of claim 1, wherein said detector is chosen from the group comprising a retina, an array detector, a quadrant detector, a photodetector, a photodiode, a charge coupled device (CCD) detector, and a photosensitive film.

17. The apparatus of claim 1, wherein said optical element is chosen from the group comprising an eye, a lens, and a mirror.

18. The apparatus of claim 17, wherein said mirror is chosen from the group comprising a spherical mirror, a segmented mirror, and a flexible mirror.

19. The apparatus of claim 1, wherein said processor comprises a computer.

20. The apparatus of claim 1, wherein said processor comprises control electronics.

21. The apparatus of claim 1 further comprising a contact lens fabrication device coupled to said processor.

22. The apparatus of claim 1 further comprising an intraocular lens fabrication device coupled to said processor.

23. The apparatus of claim 1 further comprising laser surgical equipment coupled to said processor.

24. The apparatus of claim 1, wherein said characteristic is chosen from the group comprising wavefront aberration, defocus, astigmatism, and curvature.

25. A method for determining a characteristic of an optical element, said method comprising,
   passing at least one beam of light originating from a predetermined spatial position through a lenslet in an array of lenslets to said optical element,
   subsequent to said at least one beam of light encountering said optical element, detecting said at least one beam of light at a received spatial position, and
   comparing said predetermined spatial position with said received spatial position to determine said characteristic of said optical element.

26. The method of claim 25 further comprising the step of processing said received spatial position to determine said characteristic of said optical element.

27. The method of claim 25 further comprising the step of changing said predetermined spatial position in response to said received spatial position.

28. The method of claim 25, wherein said step of detecting comprises providing a detector.

29. The method of claim 28, wherein said detector is chosen from the group comprising a retina, an array detector, a quadrant detector, a photodetector, a photodiode, a charge coupled device (CCD) detector, and a photosensitive film.

30. The method of claim 25, wherein said step of passing at least one beam of light comprises providing a spatial light pattern generator.

31. The method of claim 25, wherein said step of comparing said predetermined spatial position with said received spatial position comprises providing a processor.

32. An apparatus for generating a diffraction limited image, said apparatus comprising,
   a spatial light pattern generator adapted to generate a plurality of beams of light at selected spatial positions to compensate for a characteristic of an optical element,
   an array of lenslets adapted to receive said plurality of beams of light from said spatial light pattern generator and to direct said plurality of beams of light to said optical element, and
   an image plane positioned to receive said plurality of beams of light subsequent to said plurality of beams of light encountering said optical element and adapted to form said diffraction limited image.

33. The apparatus of claim 32, wherein each of said plurality of beams of light is coherent with respect to the others of said plurality of beams of light.

34. The apparatus of claim 32, wherein said spatial light pattern generator comprises an opaque mask having a movable aperture.

35. The apparatus of claim 32, wherein said spatial light pattern generator comprises a spatial light modulator.

36. The apparatus of claim 32, wherein said spatial light pattern generator comprises an array of light emitting elements.

37. The apparatus of claim 36, wherein said light emitting elements are chosen from the group comprising light emitting diodes (LEDs), lasers, laserdiodes, and lamps.

38. The apparatus of claim 32, wherein said spatial light pattern generator comprises a cathode ray tube (CRT).

39. The apparatus of claim 32, wherein said spatial light pattern generator comprises a liquid crystal display (LCD).

40. The apparatus of claim 32, wherein said spatial light pattern generator comprises an array of individually addressable light-modulating elements.

41. The apparatus of claim 40 further comprising a uniform light source.

42. The apparatus of claim 41, wherein said uniform light source is a laser.

43. The apparatus of claim 32, wherein said lenslet is a microlens.

44. The apparatus of claim 32, wherein said array of lenslets is arranged in a substantially uniform pattern.

45. The apparatus of claim 44, wherein said uniform pattern is chosen from the group comprising substantially a square, a triangle, a circle, a rectangle, an ellipse, a pentagon, a hexagon, an octagon, and substantially concentric circles.

46. The apparatus of claim 44, wherein said uniform pattern comprises variably placed lenslets.

47. The apparatus of claim 32, wherein said image plane comprises a detector.

48. The apparatus of claim 47, wherein said detector is chosen from the group comprising a retina, an array detector, a quadrant detector, a photodetector, a photodiode, a charge coupled device (CCD) detector, and a photosensitive film.

49. The apparatus of claim 32, wherein said optical element is chosen from the group comprising an eye, a lens, and a mirror.

50. The apparatus of claim 49, wherein said mirror is chosen from the group comprising a spherical mirror, a segmented mirror, and a flexible mirror.

51. The apparatus of claim 32 further comprising control electronics.

52. The apparatus of claim 51, wherein said control electronics comprises a processor.

53. The apparatus of claim 52 further comprising a contact lens fabrication device coupled to said processor.

54. The apparatus of claim 52 further comprising an intraocular lens fabrication device coupled to said processor.

55. The apparatus of claim 52 further comprising laser surgical equipment coupled to said processor.

56. The apparatus of claim 32, wherein said characteristic is chosen from the group comprising wavefront aberration, defocus, astigmatism, and curvature.

57. A method for generating a diffraction limited image, said method comprising, passing a plurality of beams of light through a lenslet array to an optical element, said plurality of beams of light originating from selected spatial positions to compensate for a characteristic of said optical element, and subsequent to said plurality of beams of light encountering said optical element, imaging said plurality of beams of light to form a diffraction limited image.

58. The method of claim 57, wherein each of said plurality of beams of light is coherent with respect to the others of said plurality of beams of light.

59. The method of claim 57, wherein said step of imaging comprises providing a detector.

60. The method of claim 59, wherein said detector is chosen from the group comprising a retina, an array detector, a quadrant detector, a photodetector, a photodiode, a charge coupled device (CCD) detector, and a photosensitive film.

61. The method of claim 59, wherein said step of passing a plurality of beams of light comprises providing a spatial light pattern generator.

62. The method of claim 59, wherein said step of imaging comprises providing a processor.

* * * * *